US006168804B1

(12) United States Patent
Samuel et al.

(10) Patent No.: US 6,168,804 B1
(45) Date of Patent: Jan. 2, 2001

(54) METHOD FOR ELICITING TH1-SPECIFIC IMMUNE RESPONSE

(75) Inventors: John Samuel, Edmonton (CA); Glen Kwon, Waunakee, WI (US)

(73) Assignee: University of Alberta, Edmonton (CA)

( * ) Notice: Under 35 U.S.C. 154(b), the term of this patent shall be extended for 0 days.

(21) Appl. No.: 08/737,896

(22) PCT Filed: Jun. 7, 1996

(86) PCT No.: PCT/US96/09951

§ 371 Date: Sep. 24, 1997

§ 102(e) Date: Sep. 24, 1997

(87) PCT Pub. No.: WO96/40066

PCT Pub. Date: Dec. 19, 1996

Related U.S. Application Data

(63) Continuation-in-part of application No. 08/480,499, filed on Jun. 7, 1995, now abandoned.

(51) Int. Cl.[7] .......................... A61K 9/127; A61K 39/00; A61K 45/00; A61K 47/44

(52) U.S. Cl. ................... 424/450; 424/277.1; 424/282.1; 514/13

(58) Field of Search ................................ 424/450, 277.1, 424/282.1; 514/13

(56) References Cited

PUBLICATIONS

Zhou et al Vaccine vol. 11, No. 11 (1993) pp. 1139–1144.*
Frisch et al Eur. J. of Immunol. (1991) vol 21 pp. 185–193.*
Takahashi et al J. of Immunol. (1994) vol 153 pp. 2102–2109.*
Gupta et al Vaccine 1995 vol 13 No 14 pp. 1263–1276.*

Margarian–Blander, et al. "Specific and Effective T–Cell Recognition of Cells Transfected with a Truncated Human Mucin cDNA", *Annals New York Academy for Sciences*, p. 231–243, (1993).

Gendler et al., "A Hightly Immunogenic Region of a Human Polymorphic Epithelial Mucin Expressed by Carcinomas Is Made Up of Tandem Repeats", *J. Biol. Chem.* vol. 263, No. 26, pp. 12820–12823 (1988).

Zhou et al. "Monophosphoryl lipid A enhances specific CTL induction by a soluble protein antigen entrapped in liposomes", Vaccine 1993 11(11) 1139–1144.

Brynestad et al., "Influence of Peptide Acylation, Liposome Incorporation, and Synthetic Immunomodulators on the Immunogenicity of a 1–23 Peptide of Glycoprotein D of Herpes Simplex Virus: Implications for Subunit Vaccines", *J. Virol.* vol. 64, No. 2, pp. 680–685 (1990).

Wakita et al., "Gamma–Interferon Production in Response to Hepatitis B Core Protein and Its Synthetic Peptides in Patients with Chronic Hepatitis B Virus Infection", *Digestion*, 47:149–155 (1990).

Milich et al., "Immune Response to Hepatitis B Virus Core Antigen (HbcAg): Localization of T Cell Recognition Sites within HbcAg/HBeAg1", *J. Immunol.* vol. 139, No. 4, pp. 1223–1231, (1987).

* cited by examiner

*Primary Examiner*—Geetha P. Bansal
(74) *Attorney, Agent, or Firm*—Fish & Richardson P.C.

(57) ABSTRACT

A method is provided for treating a Th1 mediated disease state by administration to a subject of a slow release vehicle such as a liposome or microsphere formulation containing an antigenic peptide and a Th1 specific immunomodulator wherein the antigenic peptide contains a T cell epitope and is released from the vehicle at a rate in the range from about 10 to 2 weight percent of the peptide in 24 hours at 37° C.

13 Claims, 19 Drawing Sheets

(A=0.9 mg/ml; B=0.175mg/ml; c=0.017 mg/ml; D=0.005 mg/ml)

METHOD FOR ELICITING TH1-SPECIFIC IMMUNE RESPONSE

CROSS REFERENCE TO RELATED APPLICATIONS

This application is a continuation-in-part application of U.S. patent application Ser. No. 08/480,499, filed Jun. 7, 1995 (ABN).

BACKGROUND OF THE INVENTION

This invention relates to slow release formulations containing peptides for use as vaccines. More particularly this application relates to liposome and microsphere formulations containing short epitope-containing peptides for raising a specific Th1 cell-mediated immune response to provide protective immunity against a disease state associated with the antigen.

BACKGROUND OF THE INVENTION

Short synthetic peptides are poor immunogens in vivo. To enhance the immunogenicity of short peptides, they are usually conjugated to large carrier proteins and associated with immunological adjuvants. However, immune responses induced by such conjugates can be mainly directed against the epitopes in the carrier proteins, and may also induce epitopic suppression. Further, alum, the only immunoadjuvant approved for human immunization, is a poor inducer of cell-mediated immune responses, which are believed to mediate rejection of certain cancers, as described by R. Bomford, "The Comparative Selectivity of Adjuvants for Humoral and Cell-Mediated Immunity," *Clin. Exp. Immunol.*, 39:435–441, 1980.

The two types of T lymphocytes that can be distinguished based on function and surface markers are helper (Th) and cytotoxic (Tc) cells. Th cells express the CD4 surface protein and upon contact with foreign antigen, activate antibody-producing B cells and Tc. Tc express the CD8 protein, and are thought to control infection by elimination of cells expressing foreign antigens. Both Tc and Th lymphocytes recognize antigens as short peptides that are bound to cell surface class I and class II major histocompatibility complex (MHC) molecules, respectively.

The mechanism by which antigens are processed into peptides differs for class I and class II MHC presentation. Antigens taken into the cell via endocytosis are digested into peptides that then bind to class II, but not class I, MHC molecules. In contrast, antigens that are synthesized within the cytoplasm or endoplasmic reticulum selectively bind to class I MHC molecules. Thus, vaccines containing subunit antigens, which gain access to only the endocytic pathway of the cell, prime the MHC class II restricted Th, but not class I restricted Tc.

Microencapsulation of antigens into liposomes has been used as an approach to enhance the immunogenicity of proteins without the use of traditional adjuvants. Liposomes in the blood stream are generally taken up by the liver and spleen, and are easily phagocytosed by macrophages, one of the primary APCs. They serve as effective vehicles for antigen delivery to macrophages. Liposomes also allow co-entrapment of immunomodulatory molecules along with the antigens, so that such molecules may be delivered to the site of antigen encounter, allowing modulation of the immune system towards protective responses.

Mucins are complex ($M_r \geq 200$ kD) glycoproteins produced by a variety of normal and malignant epithelial cells. They can be expressed as cell-surface and/or secreted molecules. Mucins comprise 50–90% (by weight) oligosaccharide structures that are linked to core peptides through O-glycosidic bonds. The core peptides of several human mucins have been characterized by cDNA cloning. Cancer-associated mucins tend to have fewer and shorter oligosaccharide structures in comparison to the normal mucins. As a result, certain core-peptide epitopes of the cancer-associated mucins can become exposed to the immune system, whereas such structures in normal mucins remain 'cryptic'. Further, the loss of polarity of cancer cells and their increased expression of mucins can also facilitate exposure of the mucin epitopes to the immune system. Thus certain 'cryptic self' epitopes of cancer-associated mucins are believed to be immunogenic in humans and have been used for immunotherapy of carcinomas. See Longenecker et al., "Prospects for Mucin Epitopes in Cancer Vaccines," *J. Tumor Marker Oncol.*, 5:11–26, 1993.

A human mucin associated with breast, ovarian and pancreatic carcinomas, MUC1, mucin, is a known potential target for active specific immunotherapy. Peptide sequences in the variable number tandem repeat (VNTR) domain of this mucin have been shown to induce humoral and cell-mediated immune responses in cancer patients. Cytotoxic T cells have been generated from lymph nodes of pancreatic, breast and ovarian carcinoma patients and have demonstrated their specificity for peptide epitopes in VNTR region of the MUC1 mucin on cancer cells. Accordingly, peptide epitopes in the VNTR domain are suitable targets for directing immune responses against MUC1$^+$ human tumors. With this in view, rodent tumor models expressing human MUC1 have been developed for evaluation of the immune responses against MUC1 sequences and their effect on tumor growth. Immunization with a recombinant vaccinia virus expressing MUC1 induced protection against tumor challenge with MUC1$^+$ tumor cells in a rat model is described by Hareuveni et al., "Vaccination Against Tumor Cells Expressing Breast Cancer Epithelial Tumor Antigen," *Proc. Natl. Acad. Sci. U.S.A.*, 87:9498–9502, 1990. The immunogenicity of MUC1 synthetic peptides showed that formulations which induced strong cell mediated immune responses inhibited tumor growth in a MUC1-transfected mouse mammary carcinoma model. More recently, V. Aspostolopoulos et al., "Immunization with Cellular and Synthetic Antigens," *Cancer Res.* 54:5186–5193, 1994, have reported that cell-mediated immune responses of "Th1 type," but not antibody responses, correlate with rejection of MUC1-transfected 3T3 cells in mice.

SUMMARY OF THE INVENTION

The present invention provides slow release antigen delivery systems that preferentially raise cell-mediated immune responses of the Th1 type against short T-cell epitope-containing peptides, for example those containing from about 11 to 34 amino acids, without the use of traditional carrier proteins and immunoadjuvants. Preferably, the peptide contains 12–25 amino acids. The antigen delivery system of this invention is a composition comprising a peptide contained within a liposome, or other slow-release delivery vehicle, that releases the peptide at a rate of less than 50 nanogram/ml/hour and preferably from about 10 to 2% of the encapsulated peptide is released over 24 hr period at 37° C.

The composition further contains a Th1 specific immunomodulatory agent associated with the slow-release delivery vehicle, preferably displayed on the surface of the delivery vehicle. The preferred Th1 specific cell mediating immunomodulator is monophosphoryl lipid A (MPLA). The compositions of this invention avoid the use of common immunomodulators completely, and exclusively use Th1 type specific immunomodulatory agents, so as to raise a specific Th1 cell mediated immune response and substantially avoid production of antibodies to the T cell antigen.

In the method of this invention, the rate of release of the antigenic peptide from the liposomal formulation into which it is encapsulated is controlled to a rate of a few nanograms per ml per hr, preferably about 10 to 2% release over a 24 hr period at 37° C. Therefore, in the practice of this invention, the liposome, or other slow release vehicle, used to encapsulate the epitope-containing peptide is selected to afford release rate characteristics that enable release of the peptide at such low rates. The very low release rate of the peptide from the liposomal formulation into the subject's body tissue and/or fluids aids in the avoidance of a humoral immune response to the antigenic peptide.

The slow-release compositions of this invention provide a vehicle effective in treatment of any disease state most effectively treated by a specific immune response of the cell-mediated Th1 type, wherein substantially no humoral immune response is raised by administration of the composition to the patient. Thus, by the practice of the methods of this invention, the problems associated with a humoral immune response in the treatment of certain disease states are substantially avoided. For instance the responses of the immune system can be focused to responses to epitopes relevant to cancer rejection, with induction of autoimmunity against self-epitopes. Important examples of disease states that can be treated by the method of this invention include cancers such as breast, pancreatic and ovarian carcinomas; viral infections such as respiratory syncytial virus; intracellular, parasitic diseases such as leishmaniasis and malaria; intracellular, bacterial diseases such as tuberculosis and leprosy; and fungal diseases such as candidiasis. Administration of immunotherapeutic or prophylactic vaccines against AIDS are also within the scope of this invention.

A BRIEF DESCRIPTION OF THE DRAWINGS

FIG. 1 is a graph illustrating the antigen specificity of Th responses in in vitro proliferation of T cells from mice immunized with liposomal formulations of various MUC1 peptides (SP1-065, SP1-070, and SP1-007), Detox™ formulations containing MUC1 peptides (SP1-007, SP1-070, AND SP1-065), a mouse mammary carcinoma cell line (410.4), the same cell line transfected to express a human MUC1 peptide as a cell surface molecule (GZHi), and an antigen free control (NO AG). The subscripts (i.e., 2500 or 1000) indicate the number of tumor cells per well used in each assay. The subscripts (i.e., 2500c or 1000c) indicate control wells to which no T cells were added.

FIGS. 2A–F are a series of graphs which compare the Th responses induced in T cells by injection of mice with a synthetic MUC1 peptides (SP1-007, SP1-065, or SP1-070), negative control peptides (SP1-037 and SP1-020) and no antigen (NO ANG) either contained in liposomal formulations (FIGS. 2A–C) or oil-water (Detox™) emulsions at a peptide dose of 3 μg/mouse (FIGS. 2D–F). The responses are recorded in counts per minute (CPM) in in vitro T cell proliferation assays.

FIGS. 3A–D are a series of graphs illustrating the effect on Th responses in an antigen-specific T cell proliferation assay of variation in dose of the synthetic peptide (SP1-065) administered in a liposomal formulation. Antigen-specific T cell proliferation was observed for immunization dose range of 100 ng to 16 μg. FIG. 3A=100 ng/mouse; FIG. 3B=5 μg/mouse; FIG. 3C=500 ng/mouse; FIG. 3D=16 μg/mouse. No specific response was detected from T cells primed with liposomes without peptide (not shown).

FIGS. 4A–D are a series of graphs illustrating the effect of the dose of monophosphoryl lipid A (MPLA) on Th responses. Antigen-specific T cell proliferation was shown in an in vitro assay of T cells recovered from mice injected with a liposomal formulation containing SP1-065 synthetic MUC1 peptide and a dose of MPLA ranging from 1 to 40 μg MPLA/mouse. FIG. 4A=1 μg/mouse; FIG. 4B=10 μg/mouse; FIG. 4C=30 μg/mouse; and FIG. 4D=40 μg/mouse of MPLA. No specific response was observed for T cells primed with liposomes at or below 1 μg (FIG. 4A).

FIGS. 5A–D are a series of graphs illustrating the influence of mouse MHC haplotype on Th responses. H-$2^b$ mice (FIG. 5A) and H-$2^{b/d}$ mice (FIG. 5D) were responders; whereas H-$2^d$ mice (FIG. 5B) and H-$2^k$ mice (FIG. 5C) were non-responders against SP1-065 antigen as the immunogen.

FIGS. 6A and 6B are graphs that illustrate antigen-specific in vitro proliferation of T cells enriched in $CD4^+$ subpopulation (FIG. 6A) and $CD8^+$ subpopulation (FIG. 6B).

FIGS. 7A and 7B are graphs comparing antibody responses induced by liposomal formulations of SP1-065 after two immunizations two weeks apart. Antigen-specific IgG (FIG. A) and IgM (FIG. B) concentrations are shown at various dilutions. The assay was conducted by direct enzyme immunoassay with the results shown as absorbance at 405 nm (background reading not subtracted).

FIG. 8 is a graph comparing the effect of liposomal charge on the encapsulation efficiency of liposomal formulations of the invention. EE=encapsulation efficiency.

FIG. 9 is a graph comparing the effect of various peptide concentrations upon the encapsulation efficiency of liposomal formulations containing MPLA on the surface and a MUC1 synthetic peptide encapsulated inside. EE=encapsulation efficiency. A=0.9 mg/ml; B=0.175 mg/ml; C=0.017 mg/ml; D=0.005 mg/ml.

(FIG. 10A) and 37° C. (FIG. 10B).

Figure 14A:
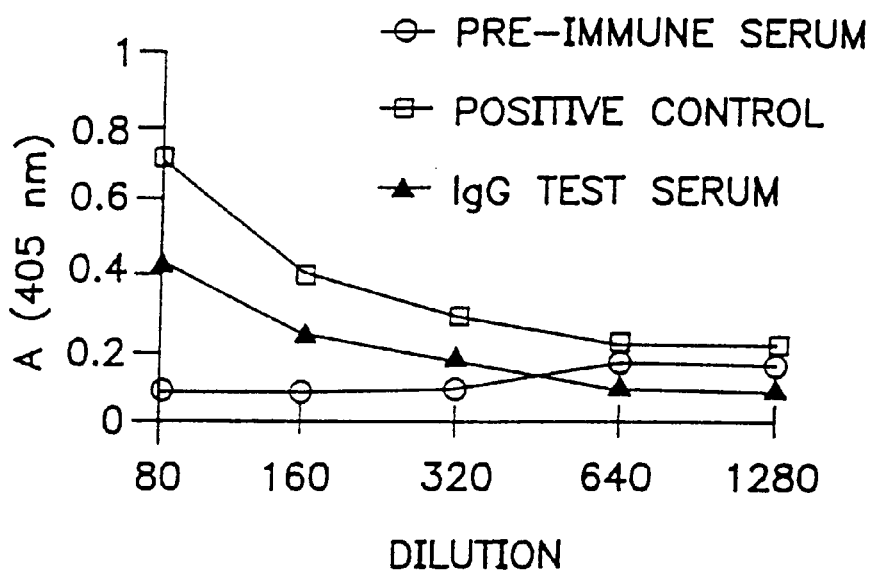
Figure 14B:
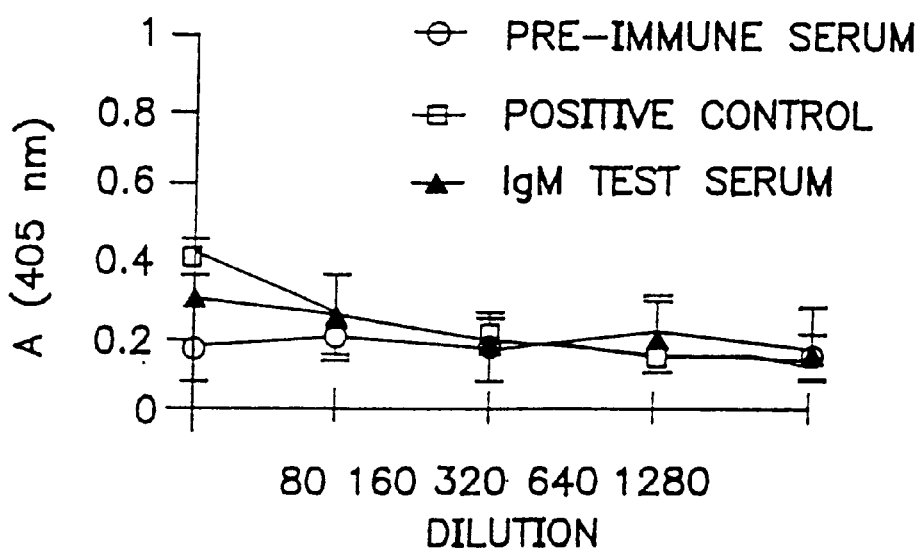

FIGS. 14A and 14B are graphs comparing antibody responses induced by microsphere formulations of SP1-065 after two immunizations two weeks apart. Antigen-specific IgG (FIG. 14A) and IgM (FIG. 14B) concentrations are shown at various dilutions. The assay was conducted by direct enzyme immunoassay with the results shown as absorbance at 405 nm (background reading not subtracted).

FIGS. 15A–D are a series of graphs showing the results of enzyme immunoassay as described in FIGS. 14A–B to analyze the antibody responses to microsphere formulations in test serum for the IgG subtypes using subtype specific secondary antibodies.

Figure 15A:
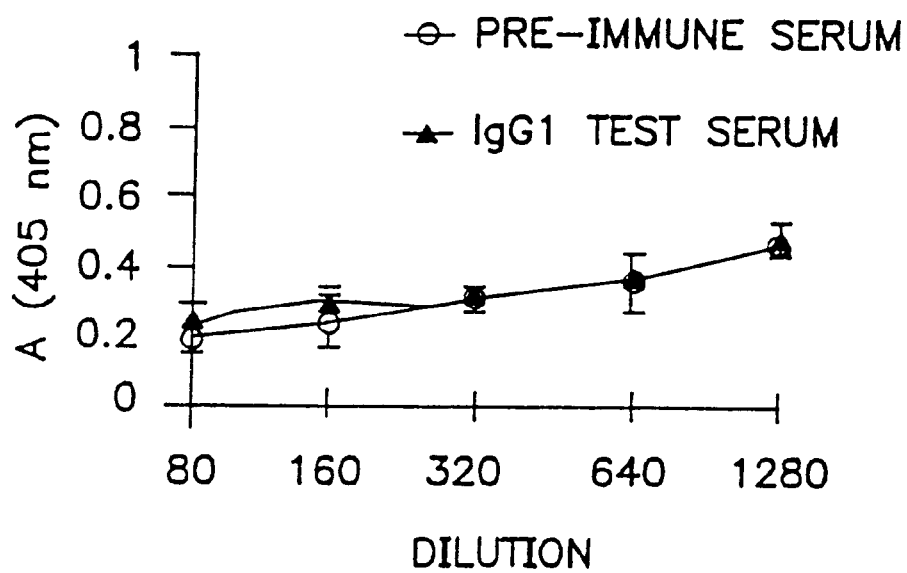

FIG. 15A shows the $IgG_1$ antibody response. o=preimmune response; ▲=$IgG_1$ response.

Figure 15B:
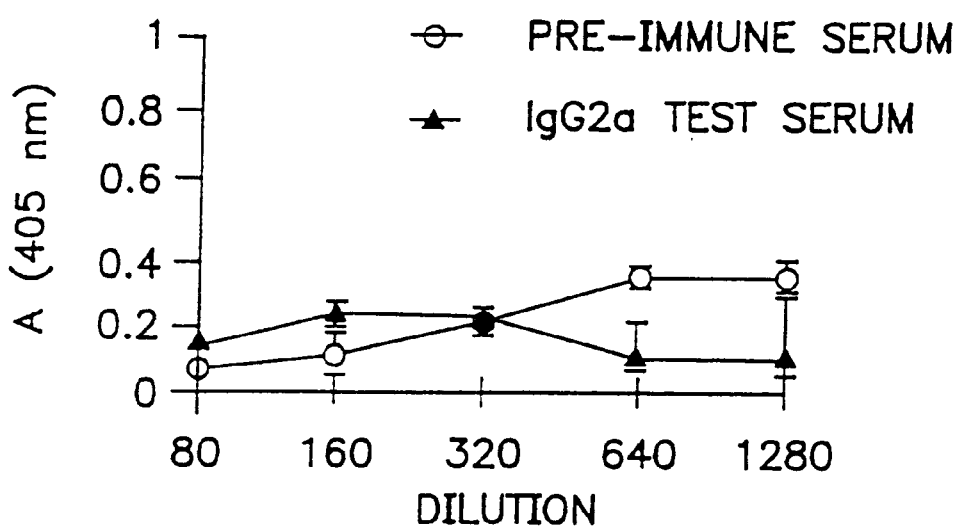

FIG. 15B shows the $IgG_{2a}$ antibody response. o=preimmune response; ▲=$IgG_{2a}$ response.

Figure 15C:
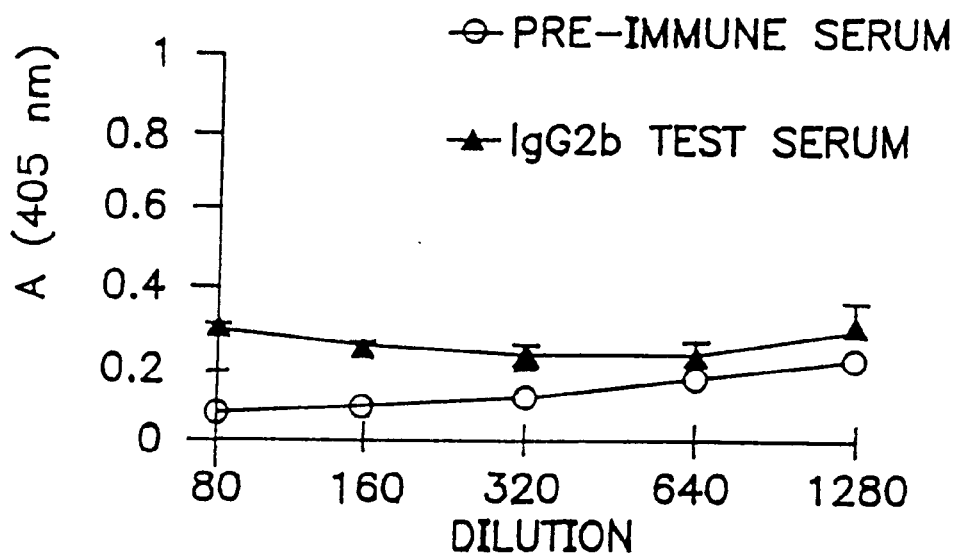

FIG. 15C shows the $IgG_{2b}$ antibody response. o=preimmune response; ▲=$IgG_{2b}$ response.

Figure 15D:
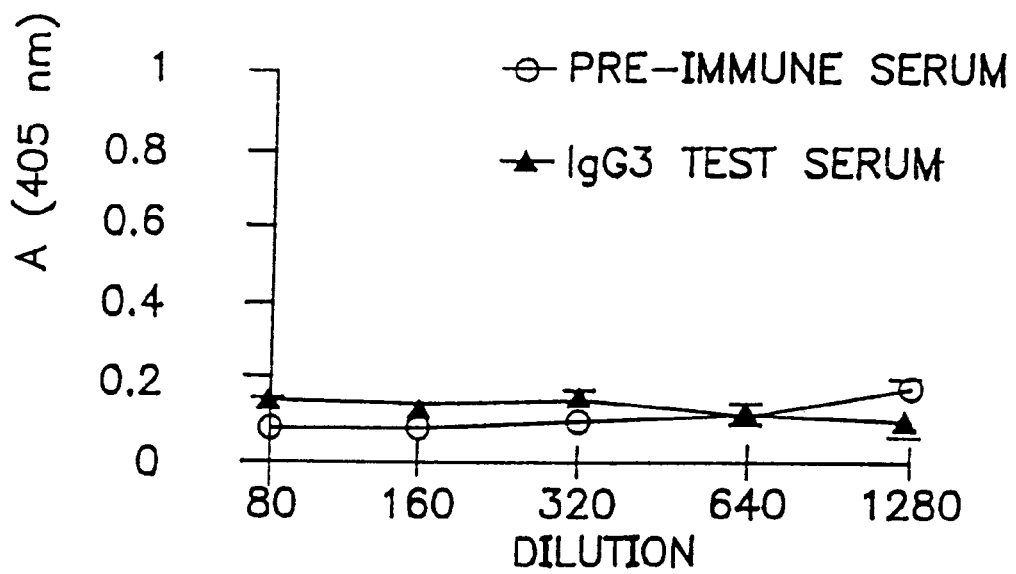

FIG. 15D shows the $IgG_3$ antibody response. o=preimmune response; ▲=$IgG_3$ response.

Figure 16:
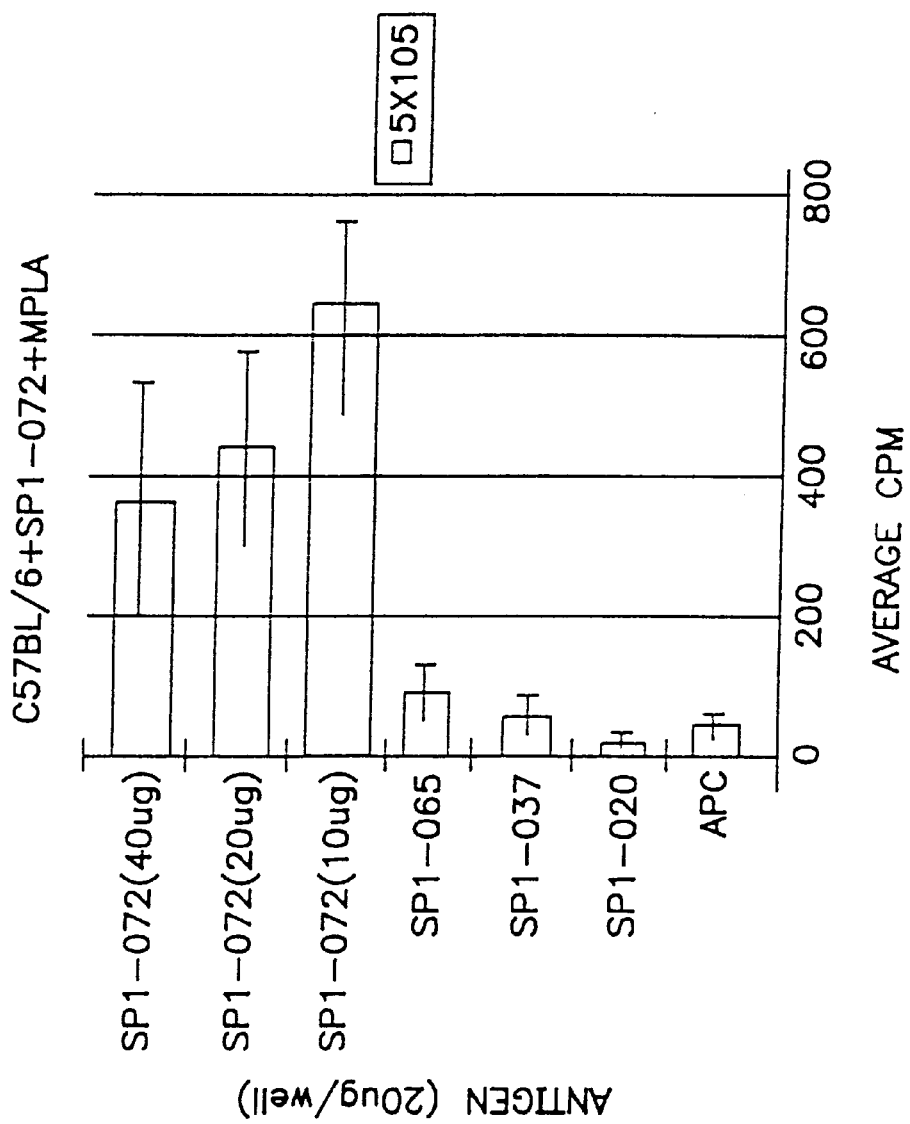

FIG. 16 is a graph showing antigen specific in vitro proliferation in CPM of T cells isolated from C57B1/6 mice immunized with collagen peptide (SP1-072) at doses of 10, 20 and 40 μg of peptide. SP1-065, SP1-037 and SP1-020 are peptides containing irrelevant T cell epitopes. APC is a negative control (background reading).

Figure 17:
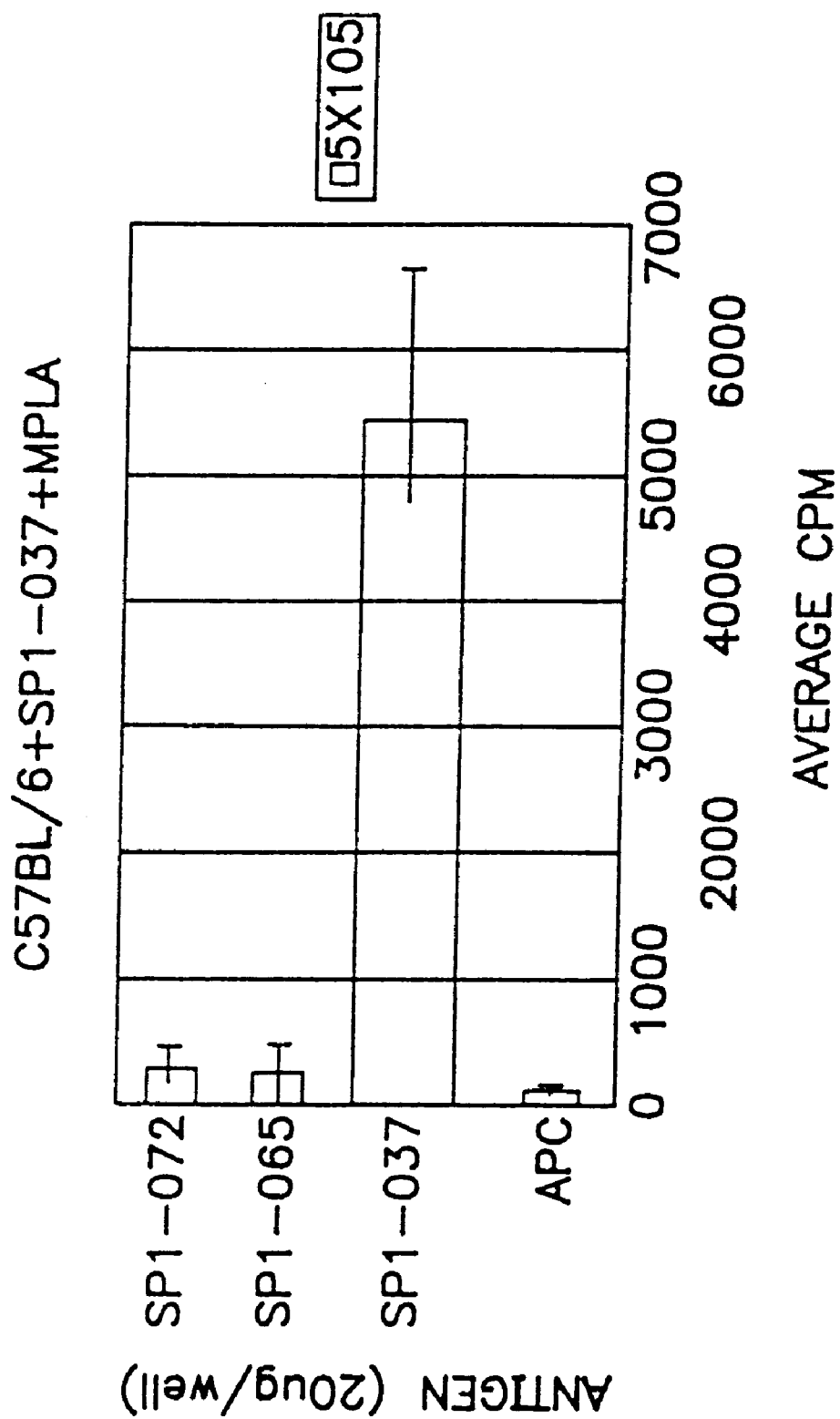

FIG. 17 is a graph showing antigen specific in vitro proliferation in CPM of T cells isolated from C57B1/6 mice immunized with ovalbumin peptide (SP1-037) at doses of 10, 20 and 40 μg of peptide. SP1-065, SP1-037 and SP1-020 are peptides containing irrelevant T cell epitopes. APC is a negative control (background reading).

A DETAILED DESCRIPTION OF THE INVENTION

Definitions

The term "antigen" as used herein refers to a molecule which is capable of immunoreactivity with an appropriate T cell antigen receptor. Antigens may comprise proteins, peptides and short oligopeptides, including synthetically produced oligopeptides, and oligopeptide mimics (i.e., organic compounds which mimic the T cell antigen receptor-binding properties of authentic immunogenic peptides, and combinations thereof.

The term "epitope" as used herein refers to the portion of an antigen that is immunoreactive with a T cell antigen receptor. T cell epitopes are most commonly short oligopeptides, or organic mimics thereof. An antigen may exhibit a number of distinct and overlapping epitopes, including B-cell and T-cell epitopes.

The size of the peptides containing epitopes of T cell antigens is based on the range reported for MHC class II binding peptides. This is commonly 12–25 residues, although longer sequences up to 34 residues, and short sequences of 11 residues have been reported (Chicz, et al., J. Experimental Medicine, 178:27–47, 1993.)

A "subject" means any vertebrate having a cell-medicated Th1 immune response, such as a human or other mammal.

An antigen is selected on the basis of the disease to be treated, or against which immunity is sought. As the present invention is designed to induce class II MHC-restricted Th1 type cell immunity, the antigens are selected based on the presence of protective epitopes. The use of short epitope-containing peptides in the practice of this invention enables introduction of the peptide directly to macrophages, and thus the peptides are made available for class II MHC presentation.

Antigens may be selected using standard methods. For example, a panel of candidate antigens may be screened with immune sera obtained from recovered or convalescent patients in order to determine which antigens contain immunodominant epitopes. T-cell haptens may be screened by exposing a patient's peripheral blood lymphocytes (PBLs) to autologous cells incubated with the hapten. The haptens bind to surface MHC proteins: immune T-cells kill the presenting cells upon recognition of the hapten-MHC complex. Systematic techniques for identifying T-cell epitopes and their mimics have been described by H. M. Geysen, U.S. Pat. No. 4,708,871.

Thus, the compositions of the invention are peptide-based vaccines for cancer and viral, bacterial and parasitic infections, especially those that are known to be best treated by a specific Th1 immune response. For treatment of certain cancers, a tumor-specific antigen that is associated with class II MHC molecules is the antigen of choice. To identify such an antigen, human tumor cells and normal cells from which the tumor was derived, both from the same individual, are obtained. Alternatively, certain tumor types have been identified which contain characteristic genetic alterations, specifically in oncogenes (e.g. ras in bladder and pancreatic cancer, BRC-2 or MUC1 in breast cancer, myc in lung cancer) or in tumor suppressor genes (e.g. p53 in colon cancer, pRB in retinoblastoma, etc.). Changes in gene expression of these genes can be created in the laboratory by transferring one of these mutated or over-expressed genes into normal human cells of the appropriate type. The method of introduction may be transection of a DNA construct which can express the mutant p53, infection with a virus which can express the mutant p53 (e.g., amphotropic retrovirus, vaccinia virus, adenovirus, etc.). Having obtained the cancer cells and corresponding normal cells, changes in gene expression may be identified using standard techniques of molecular biology, such as subtractive hybridization of tumor cell RNA using normal cell cDNA, 2D electrophoresis of proteins, followed by elution and sequencing of novel polypeptides, preparation of tumor-specific monoclonal antibodies for purification of tumor-specific proteins, or identification of cDNA clones encoding these proteins from expression libraries. Another preferred method is to obtain peptides directly from Class I antigens of the cancer cells and corresponding normal cells and to compare these peptides by HPLC as described in Grada et al., *Nature* 348:213–16, 1990; Falk et al., *Nature* 348:248–50, 1990. The sequence of these peptides can be identified or cloned using standard techniques.

When phospholipids and many other amphipathic lipids are dispersed gently in an aqueous medium they swell, hydrate, and spontaneously form multilamellar concentric bilayer vesicles with layers of aqueous media separating the lipid bilayers. These systems commonly are referred to as multilamellar liposomes or multilamellar vesicles (MLV) and have diameters of from 0.2 μm to 5 μm. Sonication of MLV results in the formation of small unilamellar vesicles (SUV) with diameters usually in the range of 200 to 500 Å, containing an aqueous solution in the core. Multivesicular liposomes (MVL) also contain multiple vesicles containing lipid bilayer, but differ from multilamellar liposomes in the random, non-concentric arrangement of the vesicles within the liposome. Amphipathic lipids can form a variety of structures other than liposomes when dispersed in water, depending on the molar ratio of lipid to water, but at low ratios the liposome is the preferred structure.

The physical characteristics of liposomes generally depend on pH, ionic strength, and the presence of cations. They characteristically show low permeability to ionic and polar substances, but at certain temperatures can undergo a gel-liquid crystalline phase (or main phase) transition dependent upon the physical properties of the lipids use in their manufacture which markedly alters their permeability. The phase transition involves a change from a closely packed, ordered structure, known as the gel state, to a loosely packed, less-ordered structure, known as the liquid crystalline state.

There are at least three types of liposomes. The term "multivesicular liposomes (MVL)" as used throughout the specification and claims means man-made, microscopic lipid vesicles comprising lipid membranes enclosing multiple non-concentric aqueous chambers with a neutral lipid separating the leaflets of a bilayer membrane. In contrast, "multilamellar liposomes or vesicles(MLV)" have multiple "onion-skin" concentric membranes, in between which are shell-like concentric aqueous compartments. Multilamellar liposomes and multivesicular liposomes characteristically have mean diameters in the micrometer range, usually from 0.5 to 25 $\mu$m. The term "unilamellar liposomes or vesicles (ULV)" as used herein refers to liposomal structures having a single aqueous chamber, usually with a mean diameter range from about 200 to 5000 Å.

Multilamellar and unilamellar liposomes can be made simply by mixing lipids into water or another aqueous solvent.

The prior art describes a number of techniques for producing ULV and MLV (for example U.S. Pat. No. 4,522,803 to Lenk; U.S. Pat. No. 4,310,506 to Baldeschweiler; U.S. Pat. No. 4,235,871 to Papahadjopoulos; U.S. Pat. No. 4,224, 179 to Schneider, U.S. Pat. No. 4,078,052 to Papahadjopoulos; U.S. Pat. No. 4,394,372 to Taylor U.S. Pat. No. 4,308, 166 to Marchetti; U.S. Pat. No. 4,485,054 to Mezei; and U.S. Pat. No. 4,508,703 to Redziniak).

In brief, multilamellar liposomal formulations for use in the practice of this invention are generally prepared simply by mixing the lipid formulation (liposome or emulsion) with the epitope-containing peptide, and permitting the mixture to incubate. The incubation period may range from 1 minute to overnight, but is generally about 18–24 hours, or overnight.

By contrast, production of multivesicular liposomes requires several process steps. Briefly, the preferred method for making MVL is as follows: The first step is making a "water-in-oil" emulsion by dissolving at least one amphipathic lipid and at least one neutral lipid in one or more volatile organic solvents for the lipid component, adding to the lipid component an immiscible first aqueous component and the peptide of the invention to be encapsulated, and optionally adding, to either or both the lipid component and the first aqueous component, an acid for modulating the release rate of the encapsulated biologically active substances from the MVL. The mixture is then emulsified, and then mixed with a second immiscible aqueous component to form a second emulsion. The second emulsion is then mixed either mechanically, by ultrasonic energy, nozzle atomization, and the like, or by combinations thereof, to form solvent spherules suspended in the second aqueous component. The solvent spherules contain multiple aqueous droplets with the substance to be encapsulated dissolved in them (see Kim et al., *Biochem. Biophys. Acta*, 728:339–348, 1983). For a comprehensive review of various methods of ULV and MLV preparation, refer to Szoka, et al. *Ann. Rev. Biophys. Bioeng.* 9:465–508, 1980.

The term "solvent spherule" as used throughout the specification and claims means a microscopic spheroid droplet of organic solvent, within which are multiple smaller droplets of aqueous solution. The solvent spherules are suspended and totally immersed in a second aqueous solution.

The term "neutral lipid" means an oil or fat that has no membrane-forming capability by itself and lacks a hydrophilic "head" group.

The term "amphipathic lipid" means a molecule that has a hydrophilic "head" group and hydrophobic "tail" group and has membrane-forming capability. Because phospholipids are found in the body, the composition of the liposome is usually a combination of phospholipids, particularly high-phase-transition-temperature phospholipids, usually in combination with steroids, especially cholesterol. Other phospholipids or other lipids may also be used. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, wherein the lipid moiety is saturated and contains from 14–18 carbon atoms, particularly from 16–18 carbon atoms. Illustrative phospholipids include egg phosphatidylcholine, dipalmitoylphosphatidylcholine, and distearoylphosphatidylcholine.

In preparing liposomes containing the peptide antigens of the invention, such variables as the efficiency of antigen encapsulation, lability of the antigen, homogeneity, and size of the resulting population of liposomes, antigen-to-lipid ratio, permeability and instability of the preparation, and pharmaceutical acceptability of the formulation should be considered (Szoka, et al., *Annual Reviews of Biophysics and Bio-engineering*, 9:467, 1980; Deamer, et. al., in *Liposomes*, Marchel Dekker, New York, 1983, 27; Hope et al., *Chem. Phys. Lipids*, 40:89, 1986).

Figure 8:
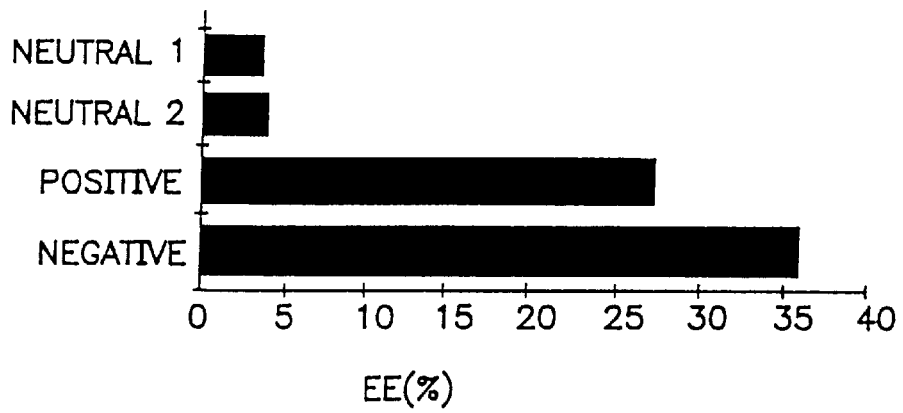
Figure 9:
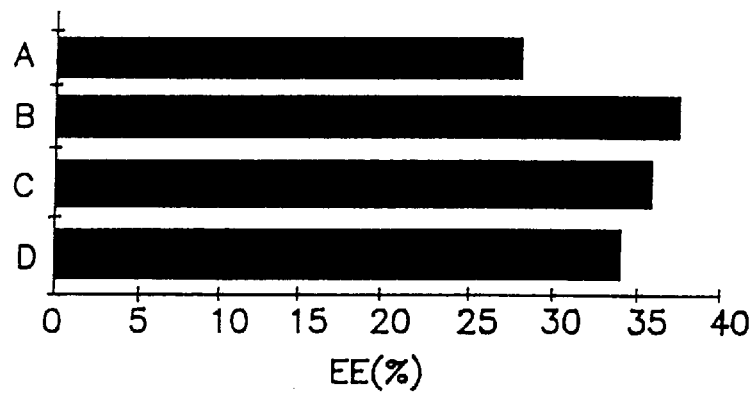

One skilled in the art will appreciate that the net charge on the liposome will influence the efficiency with which the peptide antigen is encapsulated within a liposomal formulation. As used herein, the term "encapsulation efficiency" means percentage of the total amount of peptide antigen introduced to the process for encapsulation that is incorporated into the liposome. FIG. 8 is a graph showing the effect of liposomal charge on the of liposomal formulations of the invention as determined by reverse phase HPLC. FIG. 9 is a graph showing the effect of various peptide concentrations upon the of liposomal formulations containing MPLA on the surface and from 0.005 to 0.9 mg/ml of a MUC1 synthetic peptide encapsulated inside.

The total amount of the epitope-containing peptide to be administered in a single dose will, in general, depend upon the immunogenicity of the particular antigen selected, the health of the subject, the particular condition to be treated or prevented by eliciting a specific Th1 immune response, and the release characteristics of the liposomal formulation chosen. The term an "effective amount" as used in the invention denotes that amount of the composition of this invention containing sufficient of the peptide antigen necessary to induce Th1 cells of subjects to which it is administered to specifically react with T cell epitopes present on the peptide antigen in a Th1-type immune response, without substantial B-cell response. The determination of appropriate dose ranges for any epitope-containing peptide and immunomodulator is within the level of ordinary skill in the art. However, in general the dose range of the peptide is as low as 100 ng/mouse. One skilled in the art can readily determine comparable dosages for subjects, such as humans, of any body weight, for example, in the range of 4 to 640 $\mu$g/kg of body weight. In general the dose range of the immunomodulator is in the range from about 40 to 160 ng/kg of body weight of the subject to be treated. For example, for humans ranging in weight from about 50 to 400 pounds, the dose of the immunomodulator is from about 920 ng to 39 µg.

Figure 10A:
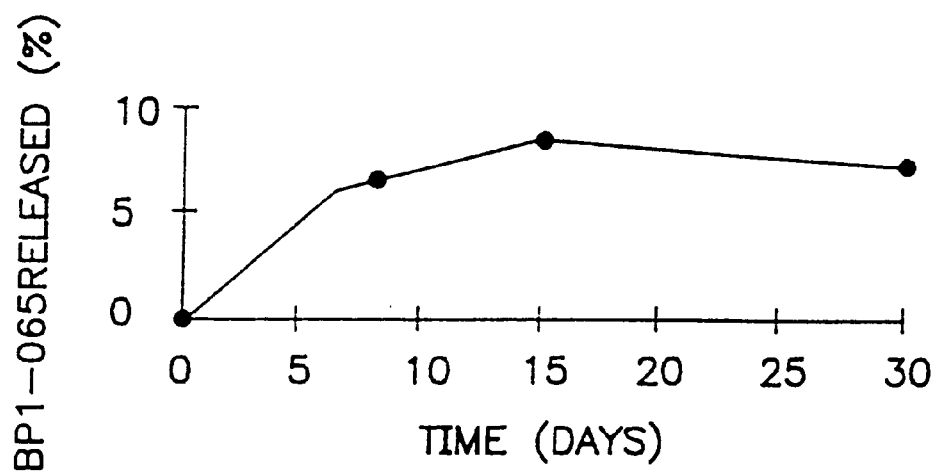
FIGS. 10A and 10B are graphs illustrating the stability over time of liposomal formulations containing MPLA on the surface and a MUC1 synthetic peptide BPI-065 stored at 40° C.
Figure 10B:
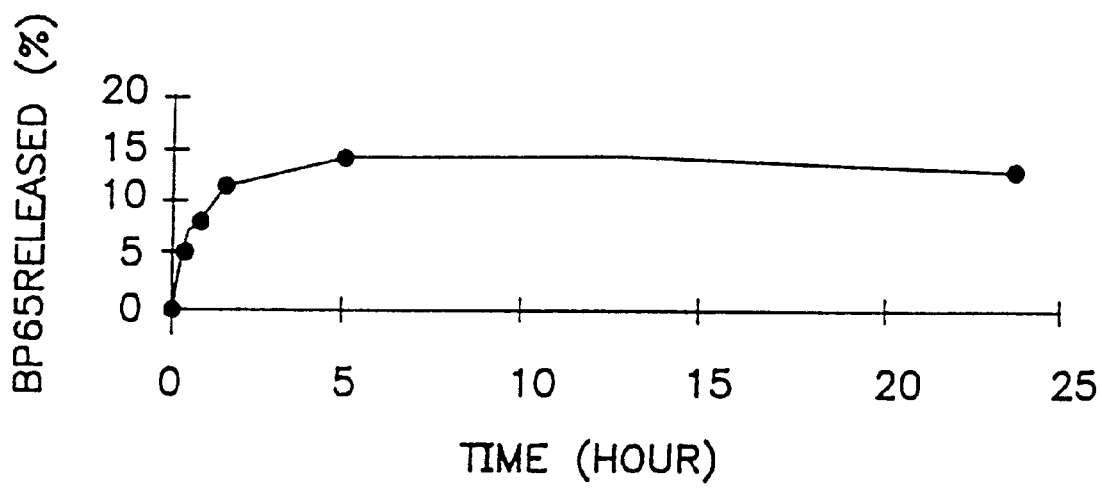

It has been discovered that the rate at which the dose is released from the vehicle is an important factor contributing to elicitation of a specific Th1 type response. Generally, it is required that the antigenic peptide be released at a rate in the range of from about 10 to 2% release over a 24 hr period at 37° C. Routine stability studies recording the rate of release at constant body temperature, which are well known in the art, may be conducted to determine the release rate of the peptide from slow release vehicles of various composition in normal saline to aid in selection of a slow release vehicle having the desired rate of peptide release. FIGS. 10A and 10B are graphs showing the results of stability studies conducted at 4° C. and 37° C., respectively, of liposomal formulations containing MPLA on the surface and a MUC1 synthetic peptide. In the practice of the method of this invention, the slow release vehicle containing the desired peptide is typically administered by parenteral means, such as by subcutaneous or intramuscular injection, or intravenous infusion. However, compositions of the invention are also suitable for administration by aerosol to the mucosa of the nose and sinuses, vagina and other membranes, for induction of mucosal immunity of the Th1 type.

Figure 7A:
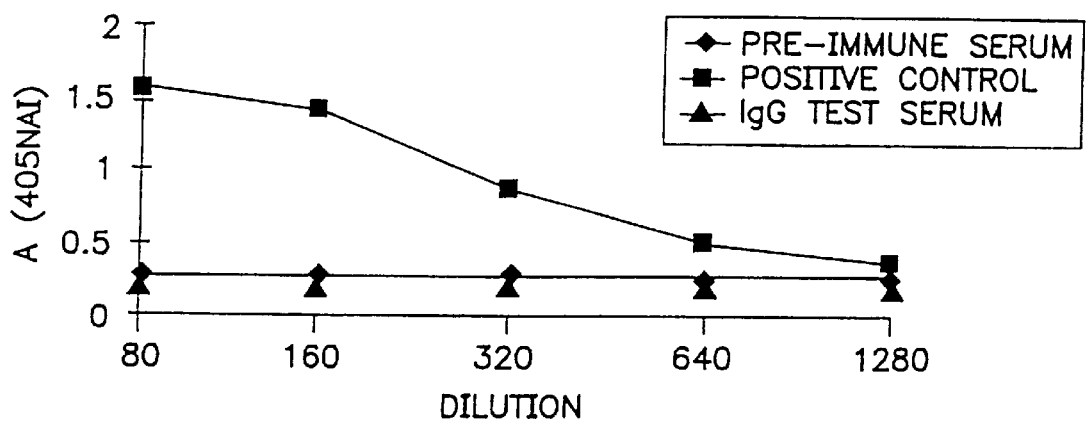
Figure 7B:
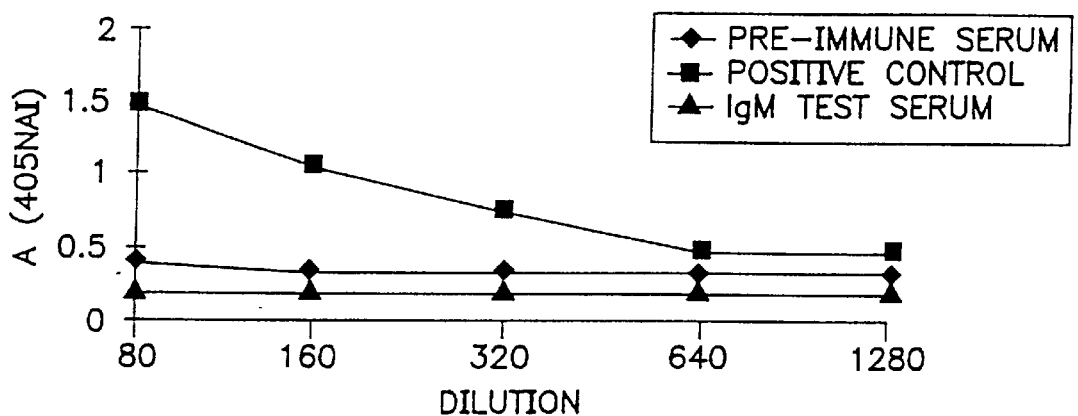

Preimmune serum samples and immune serum samples collected 12 days after the second immunization were analyzed for IgG and IgM antibody responses at various dilutions by direct enzyme immunoassays and an absorbance at 405 nm using known methods. A mouse polyclonal antiserum generated by using SP1-7-KLH as the immunogen was used as a positive control sample. FIG. 7A shows the results of the IgG assay and FIG. 7B shows the results of the IgM assay at various dilutions by direct enzyme immunoassays. Results are shown as absorbance at 405 nm (background not subtracted).

Immunogenicity of liposomal formulations of synthetic peptides corresponding to the tandem repeat domain of human breast cancer-associated antigen, MUC1 mucin, was evaluated for inducing T helper and antibody responses in mice.

Synthetic peptides corresponding to the tandem repeat region of MUC1 core peptide, encapsulated in large multilamellar liposomes containing a non-toxic Th1-specific immunomodulator, monophosphoryl lipid A (MPLA) were found to induce T helper responses in mice. The liposomal formulations of this invention successfully raise antigen-specific Th1 responses with antigenic peptide doses as small as about 4 to 640 µg/kg of body weight of the subject being treated. To accomplish a Th1 specific immune response the slow release delivery system of this invention requires three essential factors.

First, the antigenic peptide encapsulated within the delivery vehicle must contain an epitope that is recognized by T cells. Such epitopes are referred to herein as "T-cell specific epitopes." It is not necessary, however, that the T-cell epitope contained in the antigenic peptide be a Th1-specific epitope in order to generate a Th1 specific response in a subject administered the slow release delivery system of this invention, since the immunomodulator used in the slow release composition of the invention is Th1 specific and is capable of switching a Th-2 response to a Th1 response. For example, as shown in Example 11 below, a T helper response can be biased (or switched) to induce a Th1 response even when the antigenic peptide used generally induces a Th2 response.

The size of the antigenic peptide is generally large enough to accommodate the size of at least one desired T-cell epitope. However, it is also important that the peptide be small enough to escape detection by B cells to avoid undesirable stimulation of humoral immune responses. Therefore, the peptide antigens used in the slow release compositions of this invention generally range in size from about 11 to about 34 amino acids, and preferably are about 12 to about 25 amino acids in length.

One skilled in the art can readily determine whether a protein segment or polypeptide suspected of being immunogenic contains a T-cell epitope using commercially available screening techniques. T-cell epitopes are known to be generally characterized by highly conserved regions of from 11 to 34 amino acids. T cell epitopes in protein antigens can be predicted using computer programs such as SEQSEE (Wishart, et al., *CABIOS*, 10:121–132, 1994), OptiMer and EpiMer (Meister, et al., *Vaccine*, 13:581–591, 1995). These predictions are based on the amphipathicity profiles and MHC binding motifs (based on anchor residues) for different class I and class I MHC alleles (Rammensee, et al., *Immunogenetics*, 41:178–228, 1995). Since common human MHC alleles have been characterized, it is possible to make reasonable predictions about the T cell epitopes in a given antigen. Therefore, it would be possible to design a vaccine containing a cocktail of peptides to cover most if not all human MHC types.

One skilled in the art will appreciate that any given T-cell epitope may be HLA-specific or may contain segments that react with certain HLA haplotypes, but do not react with others when presented to T-cells by the antigen presenting cells. Thus, it may be necessary to screen a peptide segment selected as having a putative T-cell epitope to determine its HLA haplotype specificity using known methods.

Routine synthetic methods can be used to generate the antigenic peptides used in the slow release compositions of this invention once the sequence of a desired T-cell epitope is known. For instance, the solid phase method described by R. B. Merrifield, "Automated Peptide Synthesis," *Science*, 150:178–185, 1965, can be practiced using an automated peptide synthesizer.

A second necessary element in the slow release vehicle of this invention is the Th1 specific immunomodulator, which is associated with the liposome or other vehicle that encapsulates the peptide to hide it from the B cells of the humoral immune system. In addition to MPLA, muramyl dipeptide (MDP), muramyl tripeptide (MTP) and its derivatives such as muramyl tripeptide phosphatidyl ethanolamine (MTPE), steroids such as dehydroepiandrosterone (DHEA), plant saponins such as QS 21 all favor Th1 response (Vogel and Powell, *Pharmaceutical Biotechnology*, 6:141–228, 1995; Gupta and Siber, *Vaccine*, 13:1263–1276, 1995). It is believed that the immunomodulator is inducing the phagocytic antigen presenting cell (macrophages and dendritic cells) to secrete IL-12. Since the immunomodulator and the peptide antigen are delivered to the same antigen presenting cell, IL-12 secretion is occurring at the same microenvironment of antigen encounter by the T cells, favoring Th1 responses.

Over the last few years it has been shown that $CD4^+$ cells generally fall into one of two distinct subsets, the Th1 and Th2 cells. Th1 cells principally secrete IL-2, IFN-γ, IFN-α, IL-12 and TNFβ (the latter two of which mediate macrophage activation and delayed type hypersensitivity); while Th2 cells principally secrete IL-4 (which stimulate production of IgE antibodies), IL-5, IL-6, and IL-10. These $CD4^+$ subsets exert a negative influence on one another; i.e., secretion of Th1 lymphokines inhibits secretion of Th2 lymphokines and vice versa. In addition, it is believed that exposure of Th2 cells to CTLs also suppresses Th2 cell activity.

Thus, confirmation of the presence and quantity of the Th1 response can be determined by assaying for the presence of the cytokines associated with the Th1 response, IL-2, IFN-γ, IFN-α, IL-12 and TNFβ, using methods known in the art. Certain such means are illustrated in the Examples provided below; generally, they include immunoassays (such as enzyme linked immunosorbent assays) and immunohistological analyses performed according to techniques which are well known in the art.

How the helper T cell subsets are differentially regulated is not completely clear. Factors believed to favor Th1 activation resemble those induced by viral infection and include intracellular pathogens, exposure to IFN-γ, IFN-α, IL-2, the presence of antigen presenting cells (APCs), and exposure to low doses of antigen. Factors believed to favor Th2 activation include exposure to IL-4, and IL-10, APC activity on the part of B lymphocytes, and high doses of antigen. Active Th1 cells enhance cellular immunity and are therefore of particular value in responding to intracellular infections, while active Th2 cells enhance antibody production and are therefore of value in responding to extracellular infections. Th2 cell activity also induces IgE production through the release of IL-4.

In mice, IgG 2A antibodies are serological markers for a Th1 type immune response, whereas $IgG_1$ antibodies are indicative of a Th2 type response. Th2 responses include the allergy-associated IgE antibody class; soluble protein antigens tend to stimulate relatively strong Th2 responses. In contrast, Th1 responses are induced by antigen binding to macrophages and dendritic cells.

For use in the method of this invention, the preferred Th1 specific immunomodulator is MPLA. It is also preferred that the Th1 specific immunomodulator be attached to the surface of the slow release vehicle by any type of chemical bond or association, such as by absorption. The Th1 specific immunomodulator can also be wholly or partially incorporated into a slow release formulation, such as a liposomal formulation, so that the immunomodulator is released along with the encapsulated peptide antigen during the slow degradation of the vehicle after its injection into the subject to be treated. For example, if the slow release vehicle used to encapsulate the immunogenic peptide is a multilamellar liposome, the Th1 specific immunomodulator is preferably attached to the surface of the liposomes, but it can also be wholly or partially encapsulated within the liposomes.

A third necessary component of the slow-release composition of this invention is the slow release vehicle, which encapsulates the peptide, but slowly releases nanogram amounts of the antigenic peptide in the vicinity of the Th1 immunomodulator at a rate sufficient that the antigen presenting cells of the subject administered the composition react with the peptide and present the T-cell epitope contained therein to the subject's T cells so as to raise a Th1 specific T cell response without inducing a substantial humoral immune response. Any type of vehicle can be used so long as it sequesters the bulk of the peptide from degradation by peptidases, and affords the required slow release rate of peptide from the protection of the vehicle. For instance colloidal dispersion systems, which include macromolecule complexes, nanocapsules, microspheres, beads, and lipid-based system, including oil-in-water emulsions, micelles, mixed micelles and liposomes. However, the immunogenicity of peptides in oil/water emulsions appears to depend on factors such as the length of the peptide, adsorption of the antigen to the oil droplet, possibly through hydrophobic interactions, which may facilitate their uptake by antigen presenting cells (R. Hunter, et al., *J. Immunol.,* 127:1244–1250, 1981). Therefore, oil/water emulsions may be inefficient immunological vehicles for short peptides with hydrophilic sequences. The preferred slow release vehicles are multilamellar liposomes, as illustrated in the examples, and microspheres, for example microspheres made from poly (d,l lactic acid-co-glycolic acid), a biodegradable and biocompatible polymer approved for human use. The composition and molecular weight of the microspheres can be adjusted to ensure that release of antigen occurs intracellularly in antigen presenting cells and not prematurely at an extracellular site. The preferred composition of the microspheres is 50:50 mole ratio of d,l lactic acid and glycolic acid, and the preferred molecular weight range is 10,000–30,000 grams/mole. Methods for preparing microspheres for prolonged release of polypeptides are disclosed in U.S. Pat. Nos. 4,652,441 and 4,897,268, which are incorporated herein by reference in their entirety. Premature release of antigen from the vehicle can also be prevented by incorporating lipopeptides, such as lipid conjugated multimeric antigen peptides in an amount of 4 to 640 μg/kg.

It has been discovered that in order to raise a T cell specific response the total dose of antigenic peptide administered and the release rate of the peptide from the vehicle must be such that the animal treated is subjected to no more than about 4 to 640 μg/kg of body weight of the antigenic peptide. It is believed that the parameters analyzed included antigen specificity, effect of the dose of the peptide on the type of immune response, the effect of dose of the Th1 specific immunomodulator, the role of MHC in the mice tested, the CD4/CD8 phenotype, and the cytokine profile of proliferating T cells obtained from draining lymph nodes of mice immunized with the mutilamellar liposomes containing the Th1 specific immunomodulator, monophosphoryl lipid A (MPLA) and the test antigenic peptides.

Results of the haplotype tests indicated that MUC1 core peptide contains immunogenic Th epitopes for $H-2^b$, but not $H2^d$ and $H-2^k$ strains. The 24 amino acids peptide used in the examples of the present invention will not generate all possible sequences for binding the MHC class II molecules from the VNTR domain of MUC1. This may account for the differences in the results.

Antigen specific proliferation of T cells that were isolated from mice immunized with liposomes containing human MUC1 peptides stimulate secretion of IFN-γ, but not IL-4 or IL-10. This indicates a Th1 type of response. The lack of detectable antibody responses from the same T cells also indicates that the immune responses to the liposomal formulations of the invention were biased towards Th1 cellular response, although the exact mechanisms mediating the selectivity has not been elucidated. The selective antigen delivery to macrophages, rather than to B cells, by liposomes containing MPLA, the induction of IFN-γ secretion in the microenvironment of antigen presentation to T cells by MPLA, and the use of low doses of the peptide antigens, may act together to mediate the selective induction of Th1 response.

The following examples illustrate the manner in which the invention can be practiced. It is understood, however, that the examples are for the purpose of illustration and the invention is not to be regarded as limited to any of the specific materials or conditions therein.

EXAMPLE 1

The amino acid sequence of five MUC1 synthetic peptides and an ovalbumin control were synthesized by the solid phase method described by R. B. Merrifield, "Automated Peptide Synthesis," *Science,* 150:178–185, 1965, using an automated peptide synthesizer (Biomira Inc., Edmonton, Alberta). The sequences and abbreviations of the synthetic peptides tested are listed in Table 1 below:

TABLE 1

| SP# | ANTIGEN | SEQUENCE |
|---|---|---|
| SP1-007 | MUC1 | GVTSAPDTRPAPGSTA (SEQUENCE I.D. NO. 1) |
| SP1-020 | mouse MUC1 | DSTSSPVHSGTSSPATSAPEDSTS (SEQUENCE I.D. NO. 2) |
| SP1-023 | MUC1 | PDTRPAPGSTAPPAHGVTSA (SEQUENCE I.D. NO. 3) |
| SP1-037 | $OVA_{323-337}$ | ISQAVHAAHAEINEAGR (SEQUENCE I.D. NO. 4) |
| SPQ-065 | MUC1 | TAPPAHGVTSAPDTRPAPGSTAPP (SEQUENCE I.D. NO. 5) |
| SP1-070 | MUC1 | RPAPGSTAPPAHGVTSAPDTRPAPGSTAPP (SEQUENCE I.D. NO. 6) |

Two control peptides were included. SP1-037, which contains amino acids 323–339 of ovalbumin, and SP1-020, which contains a mouse MUC1 peptide from the murine VNTR domain having 34% homology with human MUC1 VNTR domain, as described in A. P. Spicer et al., *J. Biol. Chem.*, 266:15099–15109, 1991.

The peptides were incorporated into negatively charged multilamellar vesicles having a composition containing a ratio of 3:1:0.25 of dipalmitoyl phosphatidylcholine (DPPC) (Nippon Oil & Fats Co. Ltd., Japan): cholesterol (CHOL) (Sigma, St. Louis, Mo.): dimyristoyl phosphatidyl glycerol (DMPG) (Nippon Oil & Fats Co., Ltd. MGLS-4040) in the and ratio of 3:1:0.25 and an amount of 0.1% of the total weight of lipids of monophosphoryl lipid A (MPLA) (2 mg/ml) (Ribi Chemical Co., Inc.)

The liposomes were prepared using a rotary evaporator (HiTec RE-51) with a 250 ml round bottom flask in a water bath at 53° C. A dry ice/acetone bath was placed beneath a collecting flask connected to the rotary evaporator, and the rotary evaporator was connected to a cold water tap and to a vacuum pump through a dry ice-cold trap. To the round bottom flask was added 752 g/mol of DPPG (Nippon Oil & Fats Co., Ltd. MC-6060, 386.6 g/mol of CHOL (Sigma Chemical CH-S, St. Louis, Mo.) 688.9 g/mol (Nippon Oil MGLS-4040) and 2 mg/mL (Ribi Immunochem Co. Inc., Hamilton, Mont.). The flask was swirled to mix the contents.

The round bottom flask containing the lipids was slipped onto the rotary evaporator just above the water bath and evacuated by the vacuum pump. The round bottom flask was lowered into the water bath and rotated at about 200 rpm with the angle of the flask adjusted to assure that the lipids were beneath the water level of the bath. Simultaneously, the collecting flask was lowered into the ice/acetone bath. During rotation, the chloroform evaporated to leave a coating of lipids evenly distributed inside the flask. Then, the coated flask was covered, filled with nitrogen gas to prevent oxidation, and placed in a vacuum temperature-controlled dessicator (Precision Scientific) at 37–40° C. overnight.

In a test tube, a hydration solution of each of the test peptides was made by adding about 350 µL of a test peptide to 3650 µL of acetate buffer to yield 4 mL of liposomes. The flask was removed from the dessicator, the hydration solution was added, the flask was connected to the rotary evaporator and lowered into the water bath, and rotated at 60 rpm for 5–10 minutes to hydrate the coated lipids. A cloudy solution formed.

Encapsulation of the test peptides within the multilamellar liposomes was accomplished using the freeze-thaw method. Five freeze thaw cycles were completed using the dry ice/acetone bath and rotating the flask to freeze the liposomes under vacuum in an even thin later. Once frozen, the liposomes were allowed to thaw at room temperature and pressure for 50 minutes and then were incubated in a water bath at 41° C. between cycles. Upon completion of five freeze-thaw cycles, the contents of the flask were removed and centrifuged at 20° C. or less at 150,000×g for 20 minutes. The supernatant was decanted and subjected to HPLC analysis. The pellet was washed several times with a filter-sterilized PBS solution. The PBS solution includes 9.00 g NaCl (154 mM) (General Intermediates of Canada); 0.23 g $NaH_2O_4$ (anhydrous) (1.9 mM) (British Drug House; Toronto, Canada); and 1.15 g $Na_2HPO_4$ (anhydrous) (8.1 mM) BDH; and sufficient water to yield 1L), and was filter sterilized using 50 mm bottle top filters (0.2 micron). The supernatant was replaced with an equal volume of clean PBS, and 150 µL of the resulting solution was centrifuged for 10–12 minutes as described above. After centrifugation, the supernatant was removed, and 37.5 µL methanol was added to the pellet, and the mixture was vortexed.

The pellet was subjected to reverse phase HPLC analysis to estimate the from peptide quantitation.

EXAMPLE 2

Preparation of a Murine Cell Line Expressing Human MUC1

A mouse mammary adenocarcinoma cell line expressing human MUC1 was developed by transfection of 410.4 cells with cDNA encoding MUC1 as described by Miller et al., "Characterization of Metastatic Heterogeneity Among Subpopulations of A Single Mouse Mammary Tumor: Heterogeneity in Phenotypic Stability," *Invasion Metastasis*, 3:22–31, 1983. The cell line, designated as GZHi, was cultured in Dulbeco's Minimal Eagle's Medium (GIBCO BRL, Burlington Ontario) supplemented with fetal bovine serum (5%) and gentamycin (75 µ/ml). As shown by the data summarized in FIG. 1, expression by GZHi of MUC1 mucin as cell surface molecules was shown by in vitro proliferation of T cells eliciting antigen specific Th1 responses.

EXAMPLE 3

Determination of Antigen-Specific Proliferation of T Cells

Eight to twelve weeks-old female mice (strains C57B1/6, Balb/c, CBA, CB6/fl (C57B1/6×Balb/c)) were immunized in the thigh with the liposome formulations. Unless otherwise stated, the doses of the peptide, MPLA, and total lipids were 5 µg, 20 µg and 8 mg per mouse, respectively. The draining lymph nodes, inguinal and popliteal, were removed 9 days after a single immunization. T cells were isolated from the lymph node cells using the nylon wool purification method as described in KS Hathcock, "T Cell Enrichment by Non-Adherence to Nylon," *Current Protocols in Immunology*, pp. 3.12.1–3.12.13, 1991. The cultures were pulsed with [$^3$H]-thymidine (1 µCi/well; Amersham, Oakville, Ontario) for 24 hours. Then the cells were harvested into a glass fiber filter (Canberra-Packard Canada Ltd., Mississauga, Ontario) using the Packard Micromate cell harvester (Canberra-Packard Canada Ltd.). These filters were dried, and the incorporation of [³H]-thymidine was quantitated using a Matrix 96 Beta Counter (Canberra-Packard Canada Ltd.).

Figure 6A:
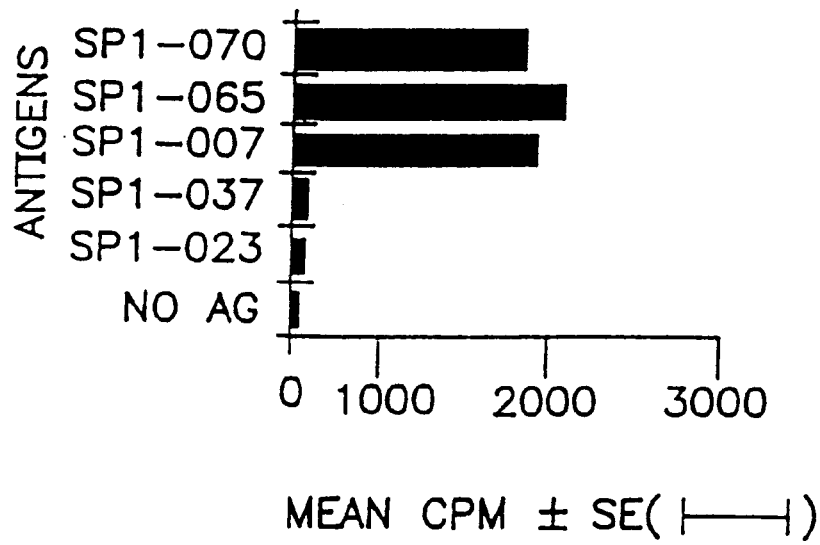
Figure 6B:
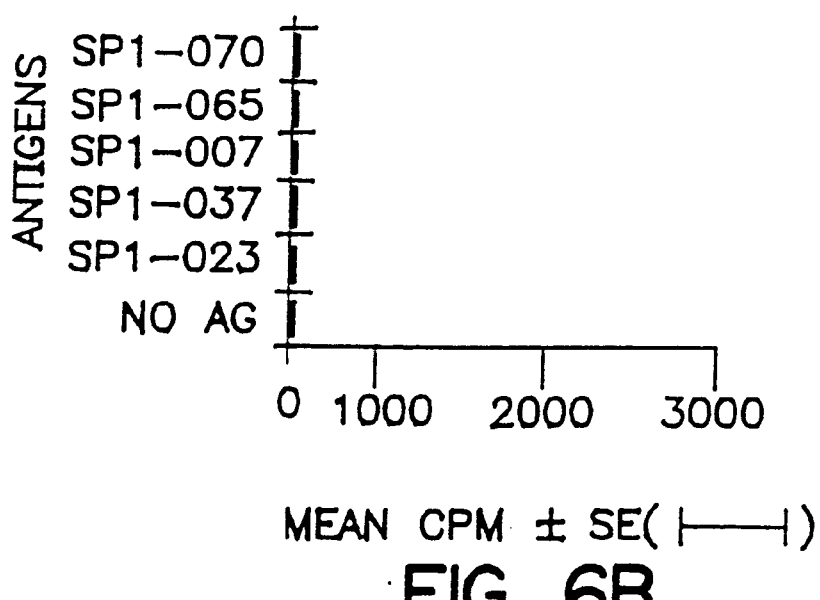

In order to characterize the proliferating T cells, T-cells isolated by the nylon wool purification method from the draining lymph nodes of immunized C57B1/6 mice were enriched for the $CD4^+$ or $CD8^+$ populations by negative selection using collect plus affinity columns (Biotex Laboratories, Edmonton, Alberta) according to the procedure provided by the manufacturer's instructions. The T cell proliferation assay was performed on each group of cells as described above. The results shown in FIG. 6 indicate that the antigen-specific proliferation was induced by $CD4^+$ T cells (FIG. 6A), and not by $CD8^+$ cells (FIG. 6B). These results indicate that the T cell proliferation was mediated by classical T helper cells.

EXAMPLE 4

Determination of Cytokines Released From Immunized Mice

Four cytokines produced by the enriched T cells were analyzed in the cell culture supernatants from proliferating T cells that were collected after 4 days. The quantities of IFN-γ, IL-2, IL-4, and IL-10 were determined by sandwich enzyme immunoassays using combinations of monoclonal antibodies (Mabs) specific for each cytokine. The combinations were as follows: R46.A2 and biotinylated XMG1.2 for IFN-γ; JES6-1a12 and biotinylated JES6-5H4 for IL-2; 11B11 and biotinylated BVD6-24G2 for IL-4; and SXC-2 and biotinylated SXC-1 for IL-10 (Pharmingen, San Diego, Calif.). The concentrations of the four cytokines in the samples were determined based on the standard curves generated using recombinant cytokine standards provided by the antibody source. The cytokine profile of the proliferating T cells is summarized in Table 2 below.

TABLE 2

Comparison of cytokines secreted by T cells

| | IMMUN-OGEN | RECALL ANTIGEN | CYTOKINE CONCENTRATION (pg/mL) | | | |
|---|---|---|---|---|---|---|
| | IN VIVO | IN VITRO | IFN-V | IL-2 | IL-4 | IL-10 |
| Liposome Formulation | SP1-007 | SP1-007 | 7,554 | 36 | 5 | 6 |
| | | No Antigen | 124 | 9 | 4 | ND |
| | SP1-065 | SP1-065 | 11,261 | 35 | 6 | 2 |
| | | No Antigen | 100 | 9 | 12 | 1 |
| | SP1-070 | SP1-070 | 9,675 | 44 | ND | ND |
| | | No Antigen | 109 | 2 | ND | ND |
| DETAX ™ Formulation | SP1-007 | SP1-007 | 134 | 14 | ND | 9 |
| | | No Antigen | 142 | 2 | ND | ND |
| | SP1-065 | SP1-065 | 78 | 6 | ND | 1 |
| | | No Antigen | 123 | 3 | 1 | 9 |
| | SP1-070 | SP1-070 | 615 | 22 | ND | 4 |
| | | No Antigen | 85 | 7 | ND | 14 |

ND: Not Detected

Figure 1:
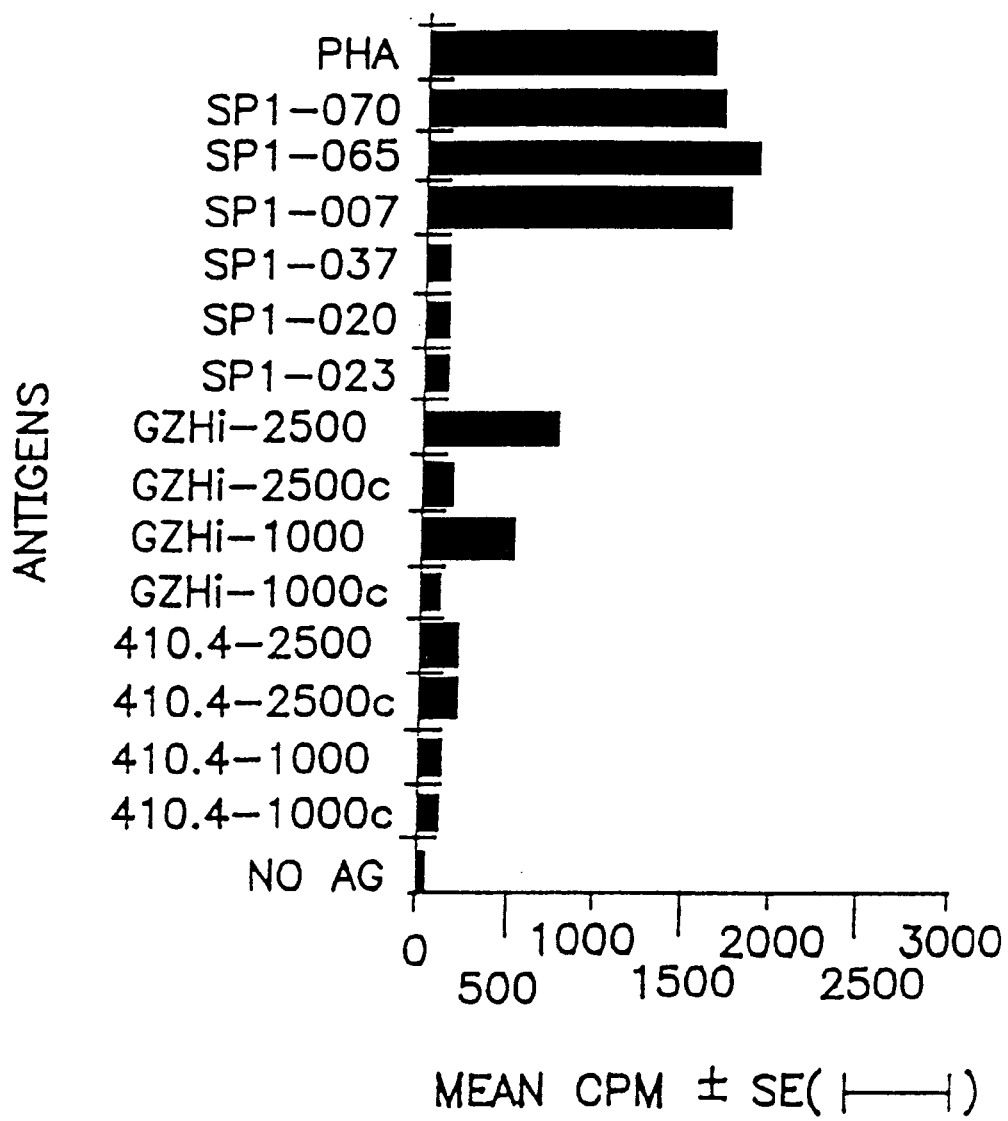
Figure 2A:
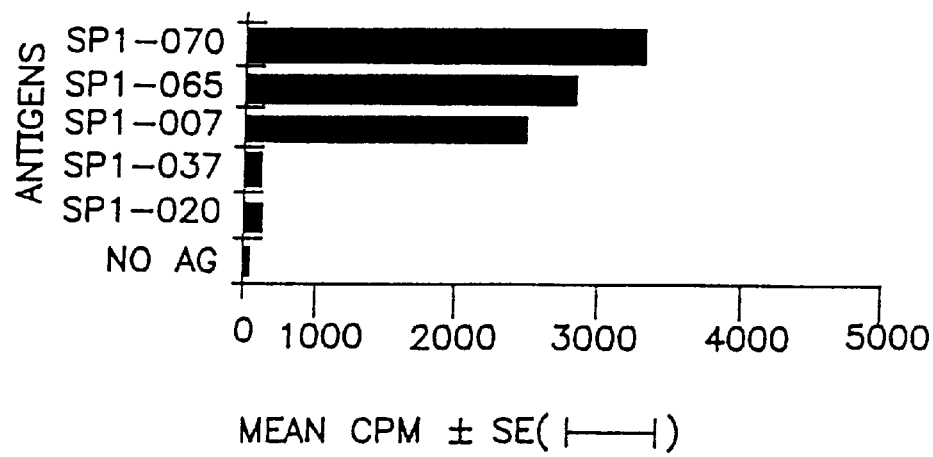
Figure 2B:
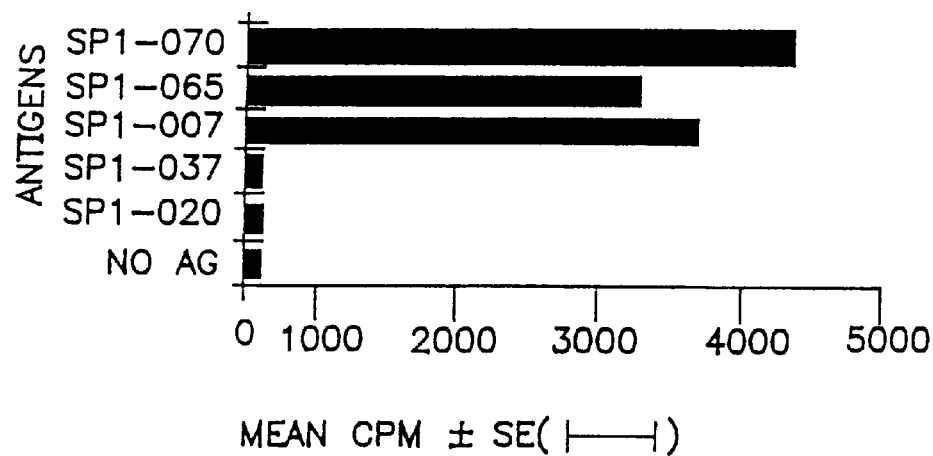
Figure 2C:
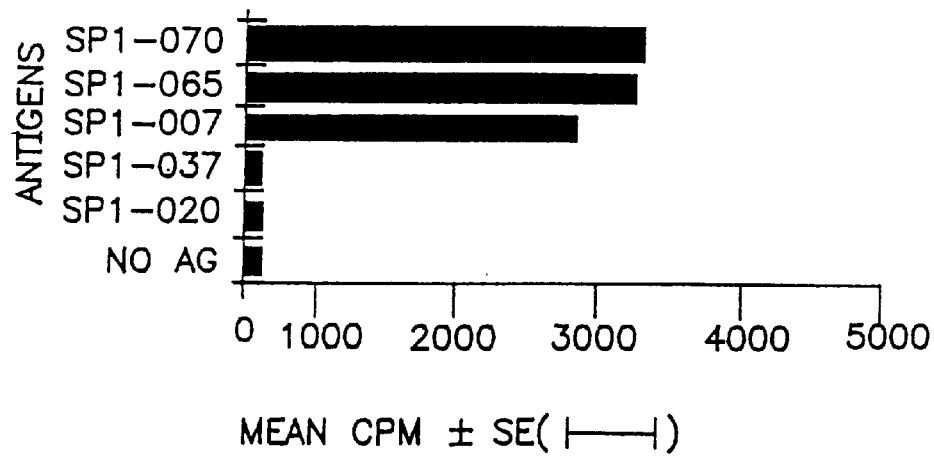
Figure 2D:
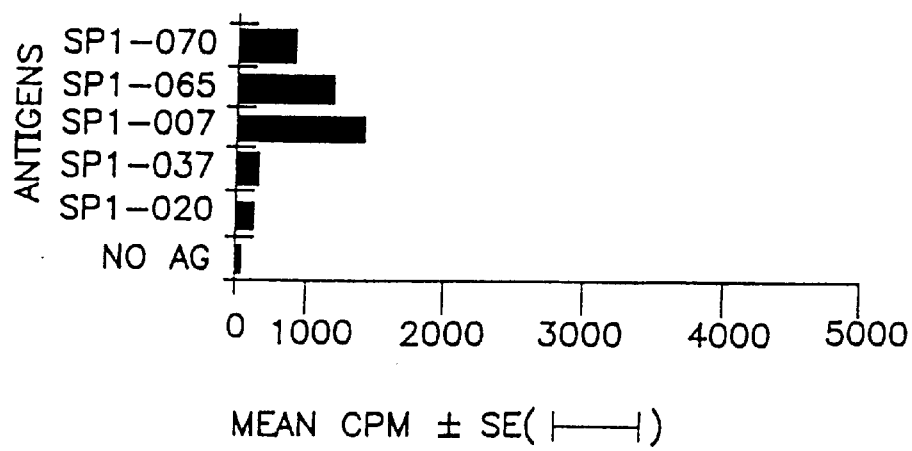
Figure 2E:
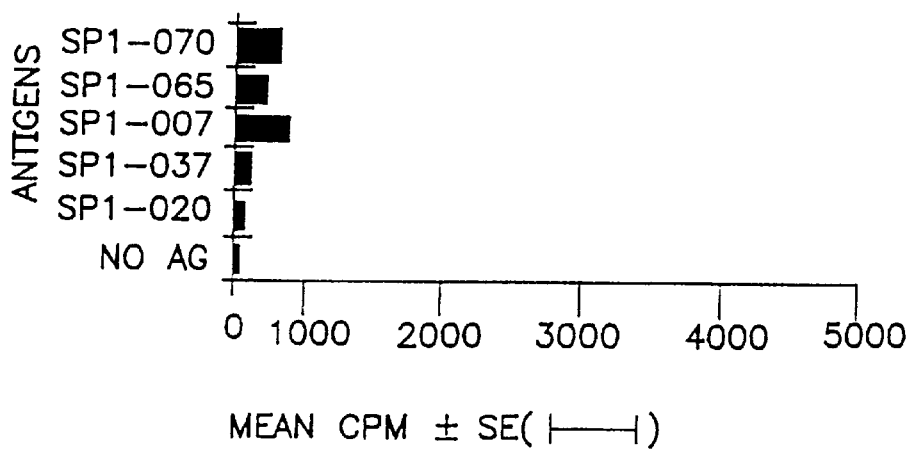
Figure 2F:
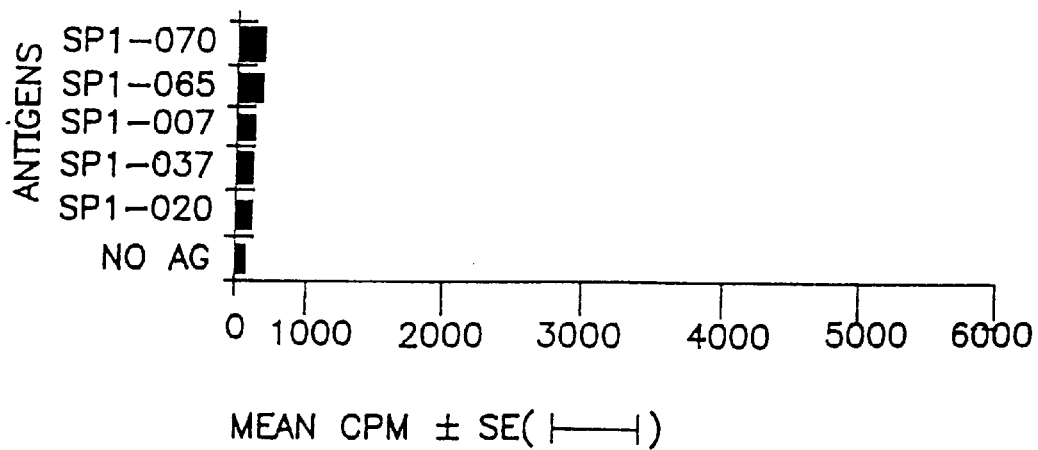
Figure 3A:
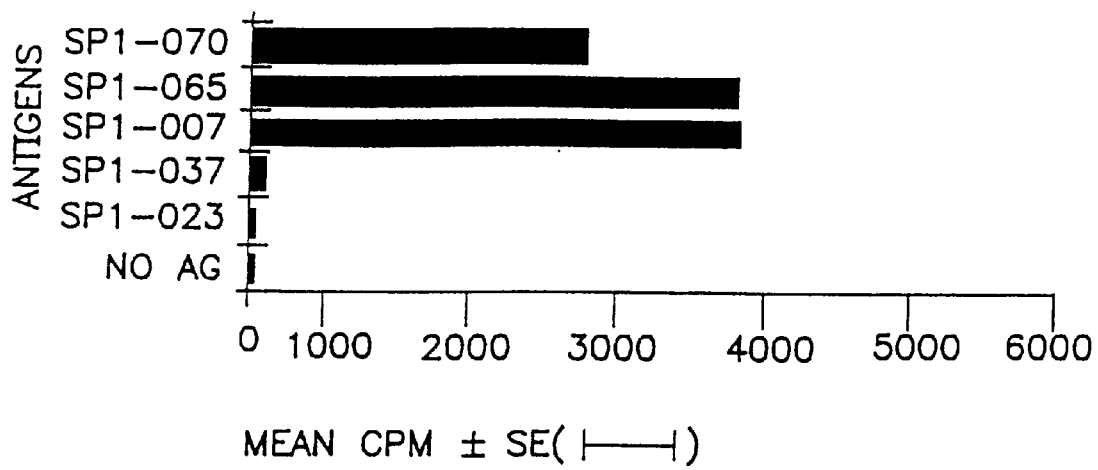
Figure 3B:
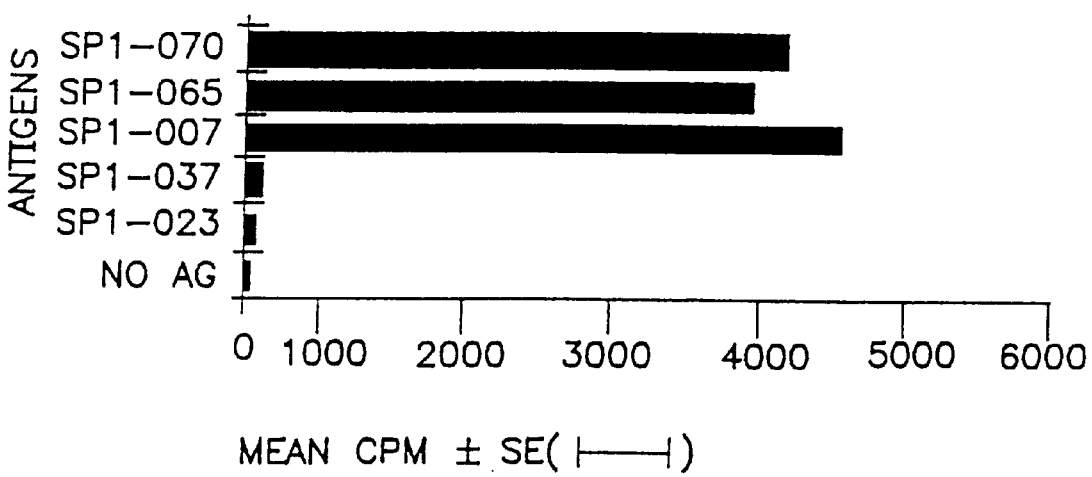
Figure 3C:
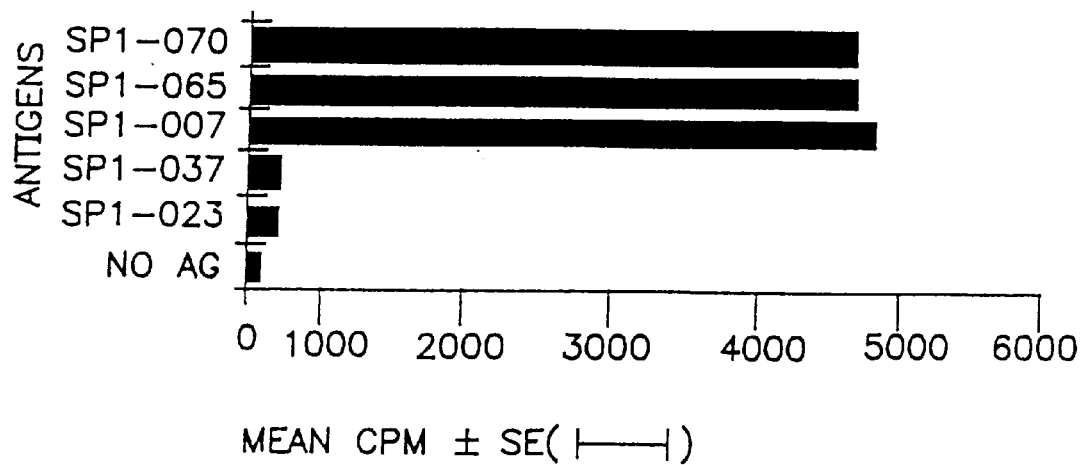
Figure 3D:
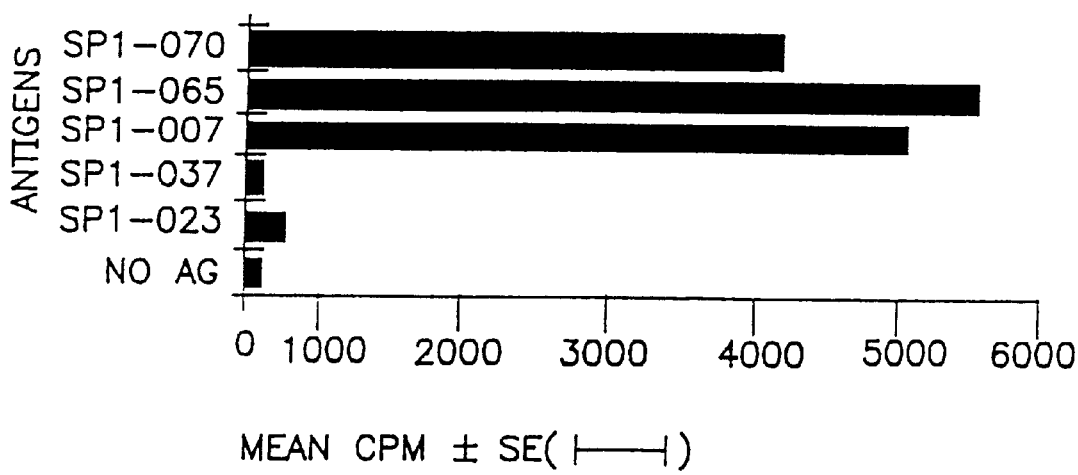
Figure 4A:
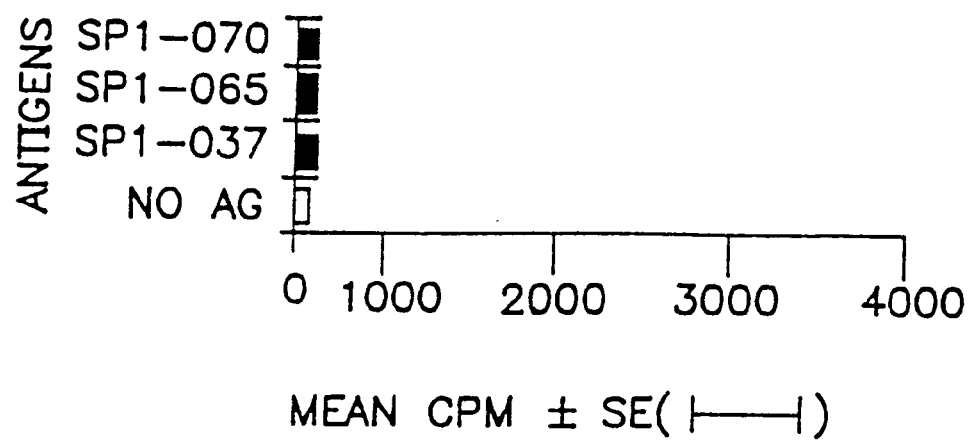
Figure 4B:
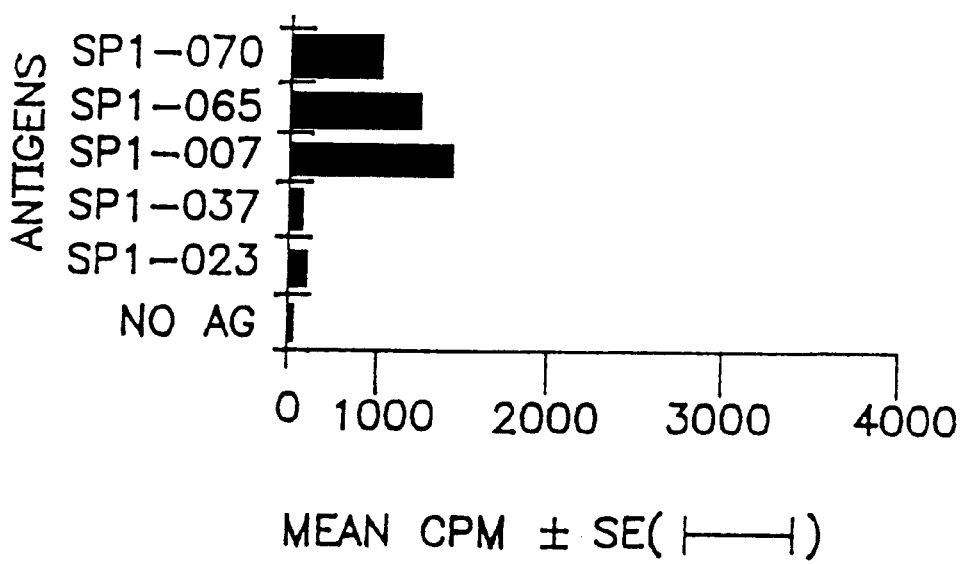
Figure 4C:
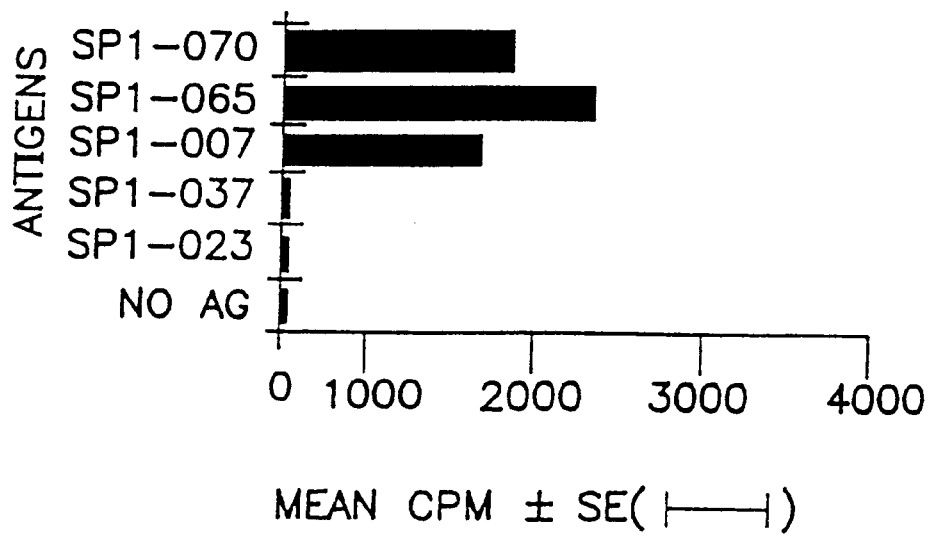
Figure 4D:
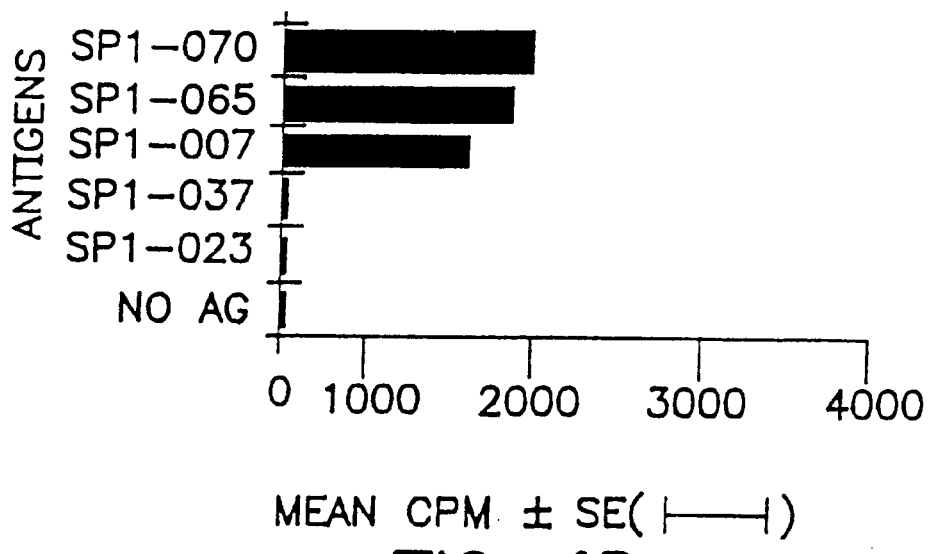
Figure 5A:
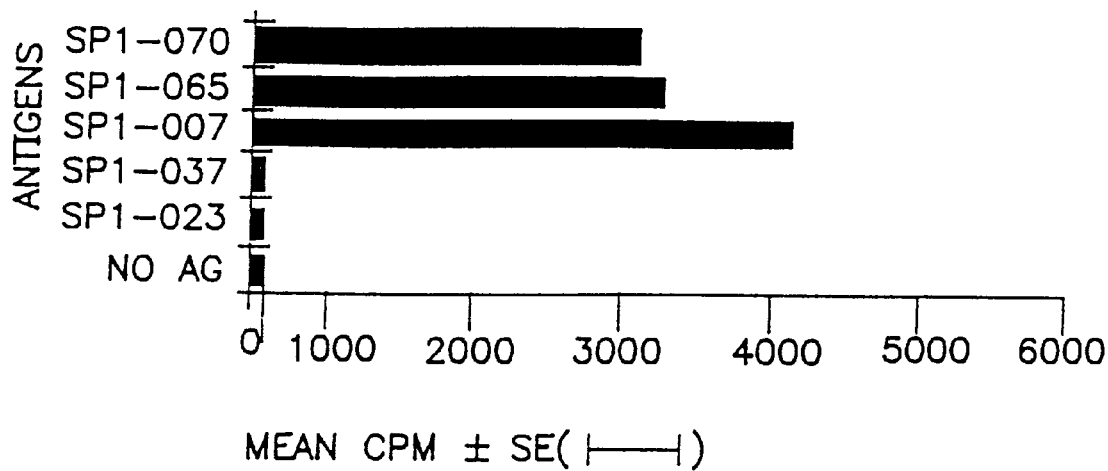
Figure 5B:
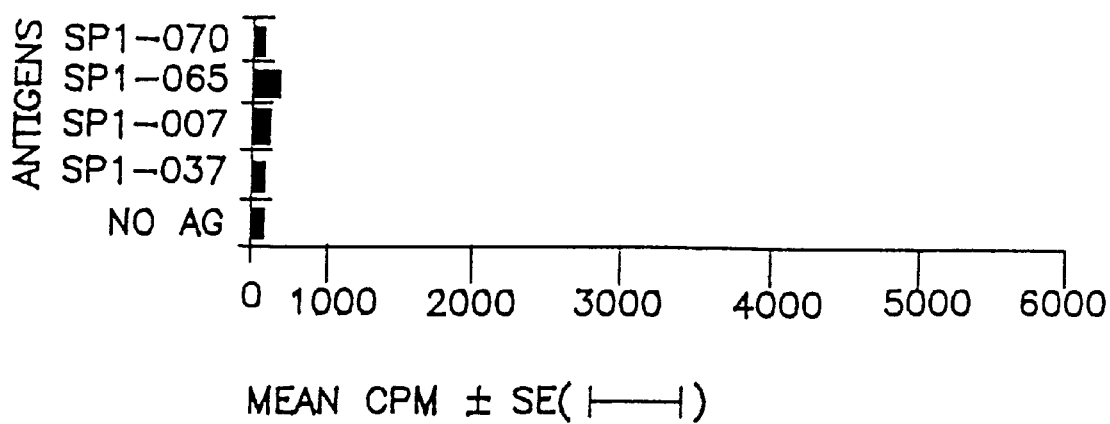
Figure 5C:
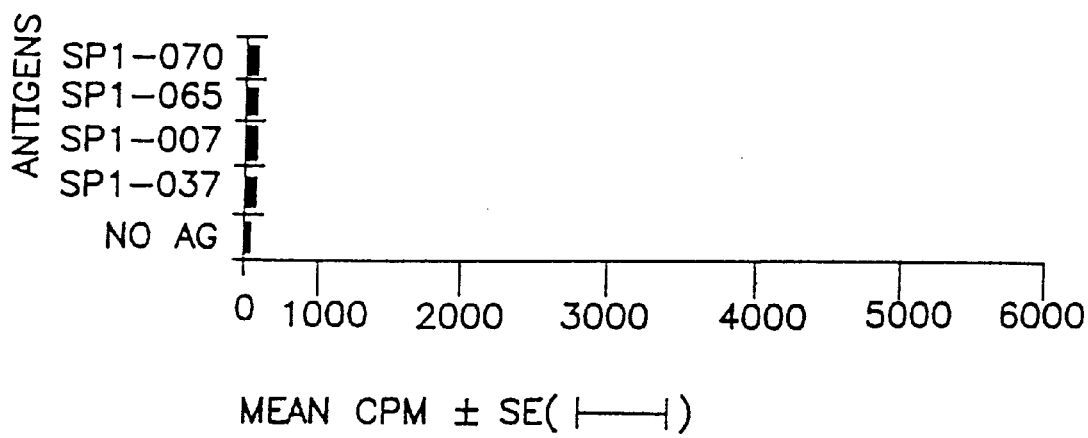
Figure 5D:
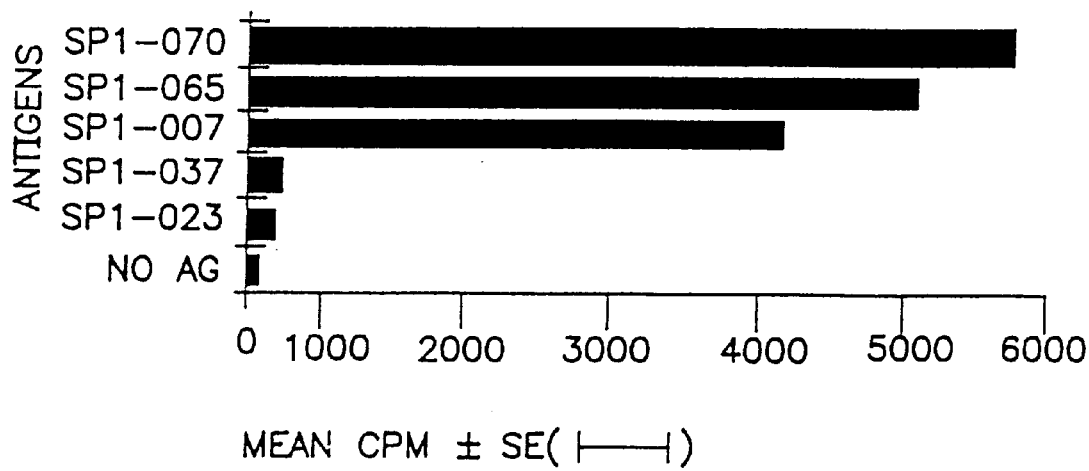

As shown by the results summarized in FIG. 1, the MUC1 peptides, SP1-007, SP1-065 and SP1-070, induced strong proliferation (24 to 71 fold above background). These results indicate that SP1-007 contains the minimal Th epitope in $H-2^b$ mice. The control irrelevant peptides, SP1-037, which contains amino acids 323–339 of ovalbumin, and SP1-020, which contains a murine MUC1 peptide from the murine VNTR domain, failed to induce any significant increase in proliferation above the background levels, demonstrating the antigen-specificity of the assay. The VNTR domain of the mouse MUC1 has 34% homology with the human MUC2 VNTR domain. One MUC1 peptide, SP-1-023, also failed to induce an antigen specific Th1 cellular immune response, indicating that this peptide does not contain the minimum sequence for the induction of T cell proliferation.

EXAMPLE 5

Determination of Antigen Specific T Cell Proliferation in Response to Naturally Expressed Peptides Similar tests were conducted to determine whether human MUC1 sequences expressed on the surface of a recombinant murine mammary cell line, GZHi, would induce specific proliferation of T cells as compared with results obtained using an untransfected parent 410.4 cell line. In order to assess the contribution of the tumor cell proliferation to the CPM of thymidine incorporated in the assay, control wells for each cell line were set with the same number of antigen presenting cells and tumor cells (for GZHi 2500c or 1000c, with c indicating control; and for 410.4 2500c or 1000c), but lacking T cells. The results of these tests are also shown in FIG. 1, and indicate that the primed T cells were able to recognize the peptide sequences of the natural MUC1 mucin expressed by GZHi cell line; whereas the parent cell line (410.4) failed to induce proliferation levels above the background level of proliferation. These results demonstrate that the liposome formulation containing the antigenic peptides induced antigen specific Th responses in vitro, and that the primed T cells were able to recognize the synthetic MUC1 peptides as well as the native peptide sequences of the natural MUC1 mucin expressed by a mammary carcinoma cell line.

After evaluation of serum samples collected from the immunized mice for their T cell responses, the serum samples were analyzed for antigen-specific antibodies by enzyme immunoassays as previously described. No detectable antibody responses (IgG or IgM at or above dilution of 1/80) could be detected in mice that received a single immunization as described in Example 3 above with the liposomal formulation. Since these immunizations were designed for T cell responses rather than humoral responses, the conditions may not have been optimal for induction of high antibody titers. In order to increase the probability for antibody production, C57B1/6 mice were given two immunizations two weeks apart using a liposomal formulation of SP1-065 having a peptide dose of 16 μg/mouse and an MPLA dose of 20 μg/mouse. The first immunization was subcutaneous, and the second immunization was interparenteral. Preimmune serum samples and immune serum samples collected 12 days after the second immunization were analyzed for IgG and IgM antibody responses at various dilutions by direct enzyme immunoassays and an absorbance at 405 nm using known methods. A mouse polyclonal antiserum generated by using SP1-7-KLH as the immunogen was used as a positive control sample. The results summarized in FIGS. 7A and 7B show that little IgG or IgM response was detected.

EXAMPLE 6

Contribution of the Liposomal Formulation to the Immune Response

To assess the importance of the slow release formulation of liposomes to the Th1 cell mediated response, a study was conducted to compare results obtained in the T cell proliferation assay of the liposome formulations as described in Example 3 with those obtained using an oil/water emulsion as the slow release formulation. Amounts of SP1-070 (30 amino acids), SP1-065 (24 amino acids) and SP1-007 (17 amino acids) equivalent to those used in the liposomal formulations described in Example 1 were formulated with a commercially available oil/water emulsion (ETOX™-B SE (stable emulsion) from Ribi Immunochemicals) as follows: The emulsions were prepared under sterile conditions and without preservatives according to the manufacturer's instructions as 10% oil in water emulsions, using squalene as the oil. The concentration of Cell Wall Skeleton (CWS) was 2500 μg/ml and the concentration of MPL® was 250 μg/ml, 2% each of lecithin and Tween 80 were added to stabilize the formulations. Three formulations were prepared: i) an active formulation containing peptide, CSW and MPL®; ii) a formulation containing peptide and MPL® but no CWS; and a placebo formulation. Aliquots of 10 ml each of the three formulations were placed into vials. The mice were injected as in Example 3 (20 μl/mouse) except that the dose of peptide contained in each injection of the formulations was 3 μg/mouse.

In vivo T cell proliferation in counts per minute (CPM) of [$H^3$]-thymidine incorporation in response to the injection of mice with the three MUC1 synthetic peptides (SP1-007, SP1-065, and SP1-070), the negative control peptides (SP1-037 and SP1-020), and no antigen (NO AG) encapsulated in liposomal formulations are shown in FIGS. 2A–C, while those in response to injection with the DETOX™ formulations of the corresponding three peptides are shown in FIGS. 2D–F. The in vitro T cell proliferation in counts per minute (CPM) in response to three MUC1 peptides, as summarized in FIGS. 2A–C, shows that all three peptides were strongly immunogenic in the liposomal formulations. By contrast, the DETOX™ formulations of SP1-070 (30 amino acids in length) was less immunogenic than the corresponding liposomal formulation. For the ETOX™ formulation of SP1-065 (24 amino acids in length) the T cell responses were weaker, and for SP1-007 (17 amino acids in length) no specific response could be noticed. These results demonstrate that the liposomal formulations of short synthetic peptides containing minimal Th epitopes can induce strong Th responses; whereas oil/water emulsion containing the same peptides in the same amounts show more variability, depending on the length or physical chemical properties of the peptides used.

The cytokines of mice immunized with the emulsion formulations are also shown in Table 2 above. As shown by these results, the secretion of IFN-γ elicited by the emulsion formulations containing MUC1 peptides of 30, 24, and 17 amino acids was substantially reduced from that raised by the corresponding liposomal formulations.

EXAMPLE 7

Effect of Dosage on Antigen Specific Immunogenicity

In order to evaluate the effect of the peptide dose on immunogenicity, C57B1/6 mice were immunized with liposomal formulations prepared as described in Example 2, but containing varying doses of encapsulated peptide. Doses of 0.1, 0.5, 5.0 and 16.0 μg/mouse were employed. As shown in FIG. 3, which summarizes the results of the in vitro T cell proliferation assays conducted as described above for the various dosage regimens, a dose as small as 100 ng/mouse was able to prime T cells in vivo for antigen specific proliferation in vitro. By contrast, T cells isolated from mice immunized with liposomes containing no peptide failed to show any antigen-specific proliferation.

EXAMPLE 8

Effect of MPLA Concentration on Antigen Specific Immunogenicity

The effect upon T-cell specific immunogenicity of the MPLA concentration in the liposomal formulations containing a MUC1 synthetic peptide SP1-065 was also evaluated using formulations containing varying amounts of MPLA. Mice were injected with doses containing 0, 1, 10, 20, and 40 ng/mouse of MPLA. The results of T-cell proliferation assays conducted as described in Example 3 above are summarized in FIGS. 4A–D. An MPLA dose of 10 ng/mouse was sufficient for effective in vivo priming of T cells against the MUC1 peptide (FIGS. 4B–D); whereas a low dose of 1 μg/mouse (FIG. 4A) was inadequate. Liposomes containing no MPLA were unable to induce Th responses. These results indicate that MPLA, the Th1 specific immunomodulator, is required to initiate the Th1 response in the mice tested.

EXAMPLE 9

Effect of Haplotype on T Helper Response

The T-cell responses of mice with different HLA haplotypes to immunization with a MUC1 peptide were compared in the in vitro T cell proliferation assay of Examples 3 and 4. The strains compared were Balb/c ($H2^d$ haplotype), CBA ($H2^k$ haplotype), C57B1/6 ($H2^b$ haplotype), and CB6/fl (C57B1/6×Balb/c) ($H2^{b/d}$ haplotype). All strains were immunized with a liposomal formulation containing SP1-065, a 24 amino acid human MUC1 peptide, and an MPLA dose of 10 ng/mouse were compared to determine whether the T helper responses are limited by the type of MHC haplotype. The results shown in FIGS. 5A–D indicate that mice having the H-$2^b$ and H-$2^{b/d}$ haplotypes (FIGS. 5B and 5C) were responders. For example, C57B1/6 ×Balb/c mice (FIG. 5D) responded equally as well as the C57B1/6 mice (FIG. 5A), but Balb/c and CBA mice (FIGS. 5B and 5C, respectively) were non-responders for the T helper responses. These results indicate that the helper T response was induced in strains having the H-$2^b$ haplotype, but in strains having the H-$2^d$ or H-$2^k$ haplotypes. The results indicate that the MUC1 core peptide contains immunogenic Th epitopes for H-$2^d$ strains. However the 24 amino acid peptide used, will not generate possible sequences for binding with MHC class II molecules from the VNTR domain of MUC1.

EXAMPLE 10

The Antigen Specificity of the T Cell Response

The performance of liposomal formulations containing the following peptides was compared using the techniques described above:

| Designation | Peptide antigen | Sequence |
|---|---|---|
| SP1-037 | $Ovalbumin_{323-339}$ | ISQAVHAAHAEINEAGR (SEQ ID NO. 4) |
| HbcAg | Hepatitis B core $antigen_{126-140}$ | IRTPPAYRPPNAPIL (SEQ ID NO. 7) |

-continued

| Designation | Peptide antigen | Sequence |
|---|---|---|
| SP1-020 | mouse MUC1 tandem repeat | DSTSSPVHSGTSSPATSAPEDSTS (SEQ ID NO. 3) |

Figure 11:
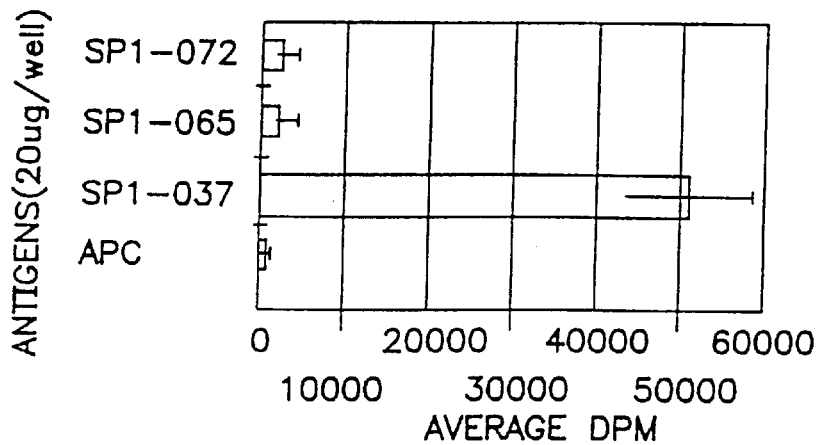
FIG. 11 is a bar graph showing antigen specific T-cell proliferation evaluated by in vitro $^3$H-thymidine incorporation assay against SP1-037, a synthetic peptide contain amino acids 323-339 of the ovalbumin protein. Control peptide SP1-065, is a 24 amino acid segment of the human MUC1 protein, and control peptide SP1-072 is a 20 amino acid segment of the human collagen peptide.
Figure 12:
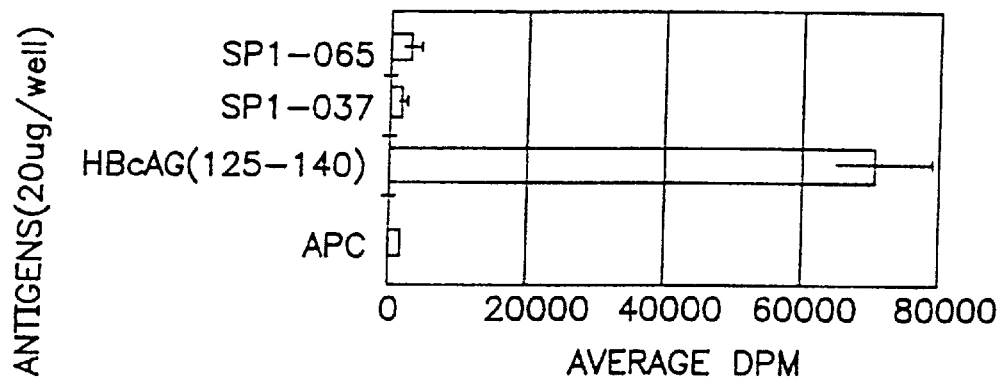
FIG. 12 is a bar graph showing antigen specific T-cell proliferation against HBcAG, a synthetic peptide containing amino acids 126–140 of the Hepatitis B core antigen. Control peptide SP1-037 is a segment containing amino acids 323–339 of the ovalbumin protein, and control peptide SP1-065, is a 24 amino acid segment of the human MUC1 protein.
Figure 13:
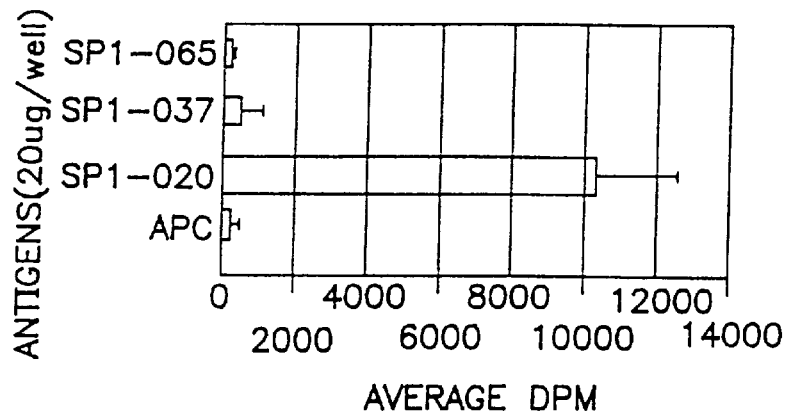
FIG. 13 is a bar graph showing antigen specific T-cell proliferation against SP1-020, a synthetic peptide containing a 24 amino acid segment of the mouse MUC1 peptide.

Briefly, the peptides were encapsulated in liposomes containing monophosphoryl lipid A as described in Example 1. C57 BL/6 mice (HLA: H-$2^b$) were immunized subcutaneously, lymphnodes were removed on day 9, T cells were isolated, and antigen-specific proliferative responses were evaluated by in vitro $^3$H-thymidine incorporation assay using specific peptides and irrelevant negative control peptides. The results of these studies, as shown in FIGS. 11, 12 and 13 indicate that an antigen-specific immune responses of the Th1 type was raised against each of the peptides, with the non-specific peptides serving as controls. In each case, the specific peptides induced significantly higher proliferative responses above the background responses (shown as APC) in comparison to those of irrelevant peptides.

Successful induction of T cell responses against mouse MUC1 also demonstrates effectiveness of the delivery system in inducing immune responses against the background of self-tolerance against this peptide in mice. This is of particular significance in the design of cancer vaccines since most of the antigens used for cancer vaccine design are self antigens, and the delivery system should be effective in breaking self-tolerance against such antigens. The HBcAg peptide used in this study was previously shown to induce a Th2 type of response in H-$2^b$ mice when administered in complete Freund's adjuvant (D. R. Milich et al., J. Virol. 69:2776, 1995). The results shown in FIG. 12 indicate that the slow release delivery system of this invention was able to shift the Th2 response to a Th1 response.

The cytokine profiles of the proliferating T cells against the ovalbumin and hepatitis B peptides were also determined as described above in Example 4. The results of the cytokine studies for SP1-037 and HBcAg, summarized in Tables 3 and 4, respectively, showed high production of IFN-γ, but levels of IL-4 and IL-10 scarcely above background (shown as APC).

TABLE 3

|  | IFN-γ pg/mL | IL-4 pg/mL | IL-10 pg/mL |
|---|---|---|---|
| APC | Trace | Trace | Trace |
| SP1-037 | 114,000 | Trace | 112 |
| SP1-065 | Trace | Trace | Trace |

Trace = below minimum detection limit
Minimum detection limit for IFN-γ is 156 pg/mL
Minimum detection limit for IL-4 is 52 pg/mL
Minimum detection limit for IL-10 is 50 pg/mL

TABLE 4

|  | IFN-γ | IL-4 | IL-10 |
|---|---|---|---|
| APC | Trace | Trace | Trace |
| SP1-037 | Trace | Trace | Trace |
| HbcAg | 5685 | Trace | 294 |

Trace = below minimum detection limit
Minimum detection limit for IFN-γ is 156 pg/mL
Minimum detection limit for IL-4 is 52 pg/mL
Minimum detection limit for IL-10 is 50 pg/mL

EXAMPLE 11

In order to examine the general applicability of slow release delivery systems for delivery of peptide-based vaccines in general, two additional peptides were evaluated for T helper responses using the T cell proliferation assay and cytokine quantitation procedures disclosed in Examples 3 and 4 above.

| Designation | Peptide antigen | Sequence |
|---|---|---|
| SP1-072 | Human collagen (IV) ($\alpha 2_{675-694}$)[1] | EAIQPGCIGGPKGLPGLPGP (SEQ ID NO. 8) |
| SP1-037 | Ovalbumin$_{323-339}$ | ISQAVHAAHAEINEAGR (SEQ ID NO. 4) |

[1]Amino acid sequence disclosed in J. S. Murray et al., Eur. J. Immunol., 24:2337–2344, 1994.

The ovalbumin peptide potentially induces either a Th1 or a Th2 response, and the collagen peptide usually induces a Th2 type of response.

C57BL/6 mice were immunized using the MPLA containing multivesicular liposome formulation having a dose of 1 μg of peptide per mouse. T cells were primed in vivo for antigen specific proliferation in vitro as determined by the T cell proliferation assay. As shown in FIG. 14, SP1-072 antigen induced antigen-specific proliferation in vitro, while irrelevant peptide antigens such as SP1-065 and SP1-037 and SP1-020 induced no significant proliferation above background. Similarly, immunization with SP1-037 (ovalbumin) also primed T cells in vivo for antigen-specific proliferation in vitro, as show by the results summarized in FIG. 17. 5P1-037 antigen induced strong proliferation in vitro, while irrelevant peptides such as SP1-072 and SP1-065 induced no proliferation.

Results of the analysis of the cytokines secreted during the T cell proliferation assay as shown in Table 5 below, indicate that the antigen specific proliferation in both experiments was associated with secretion of IFNγ, but not IL-4 or IL-10. This cytokine profile shows that the proliferating cells were of the Th1 type.

TABLE 5

| SP1-037 + MPLA | IL-10 | IL-4 | IL-2 | IFN-γ |
|---|---|---|---|---|
| APC | 9 | ND | 0 | ND |
| OVA | 7 | ND | 10 | 298 |
| HSA | 16 | ND | 20 | 423 |
| SP1-037 | 112 | ND | 43 | 23965 |
| SP1-065 | 7 | ND | 11 | 75 |
| SP1-072 | ND | ND | 0 | 51 |
| CON A (CONCANAVALIN A) | 19 | ND | ND | 7496 |

| SP1-072 + MPLA | IL-10 | IL-4 | IL-2 | IFN-γ |
|---|---|---|---|---|
| APC | 14 | ND | 5 | 38 |
| HSA | 13 | ND | 10 | 84 |
| SP1-020 | 12 | ND | 4 | ND |
| SP1-037 | 12 | ND | 5 | ND |
| SP1-065 | ND | ND | ND | ND |
| SP1-072 (10 μg/well) | ND | 7 | 2 | 709 |

TABLE 5-continued

| | | | | |
|---|---|---|---|---|
| SP1-072 (20 μg/well) | ND | 7 | 11 | 724 |
| SP1-072 (40 μg/well) | 2 | 10 | 10 | 578 |
| CON A (CONCANAVALIN A) | 21 | 12 | 10 | 2272 |

In the case of the collagen peptide, the magnitude of the T cell proliferation and IFN-γ secretion was much lower than that for the ovalbumin peptide. This is due to the lower affinity of the peptide for the class II MHC molecules of the H-$2^b$ mice. As shown by the data summarized in FIG. 16, a higher level of proliferation could be elicited by changing the dose of BP1-072 peptide to 10 μg/mouse, but dosages of 20 μg and 40 μg of BP1-072/mouse caused the response to decrease.

This experiment demonstrates the general application of the slow release formulations of the invention for peptide-based vaccines without the use of traditional carrier proteins and adjuvants, such as alum. Using these formulations, the T helper responses can be biased (or switched) to induce a Th1 type of response even when the peptide used (as in the case of the collagen peptide) usually induces a Th2 type of response.

EXAMPLE 12

Comparisons were made between the liposomal formulation described in Examples 1–5 and a formulation of biodegradable microspheres to determine the immune response generated against MUC1 peptides (SP1-007, SP1-023, SP1-065, SP1-070) when administered in a biodegradable microsphere containing MPLA immunomodulator.

Procedure 100 mg of poly(d,l lactic acid-co-glycolic acid) (PLGA) 50:50 was dissolved in 400 μl of CHCl$_3$ and added to 100 μl of monophosphoryl-lipid A (MPLA) a chloroform solution (2.0 mg/ml). 8.0 ml of 9.0% w/v polyvinylalcohol (PVA) was placed in a beaker and stirred with a magnetic stirrer. After dissolution of the PLGA in CHCl$_3$, 50 μl of peptide aqueous solution (2 mg/ml) was added to the PLGA solution. This mixture was shaken by hand for 5 sec and sonicated for 15 sec at level 4 to form the first emulsion.

2.0 ml of 9.0% w/v PVA was added to the first emulsion. This mixture was agitated by hand for 5 sec followed by sonication for 20 sec to ensure formation of the secondary emulsion. The secondary emulsion was then transferred to the 8.0 ml of stirring 9.0% w/v PVA and continued to be stirred for 2–3 h to allow for evaporation of the CHCL$_3$.

After 2 h of stirring, the 2° emulsion was diluted two fold with distilled H$_2$O to decrease the viscosity of the emulsion. The microspheres were then collected via centrifugation using an ultracentrifuge set at 20° C., 20,000 rpms for 10 min. The microspheres were then washed twice with distilled H$_2$O to remove any residual PVA followed by centrifugation under the previously stated conditions.

The PLGA microsopheres loaded with peptide and MPLA were then freeze-dried for 2–3 days.

A profile of cytokines produced by proliferating T cells obtained from draining lymph nodes of mice immunized with the microspheres containing the Th1 specific immunomodulator, monophosphoryl lipid A (MPLA) and the test antigenic peptides is shown in Table 6 below, which contrasts the microsphere results with the liposome results.

TABLE 6

Comparison of cytokines secreted by T cells, primed in vivo with liposomes or microsphere formulations of MUC1 peptides, in response to peptide challenge in vitro.

| IMMUNOGEN | | RECALL ANTIGEN IN VITRO | CYTOKINE CONCENTRATION (pg/mL) | | | |
|---|---|---|---|---|---|---|
| | IN VIVO | | IFN-γ | IL-2 | IL-4 | IL-10 |
| Liposome Formulation | SP1-065 | SP1-007 | 7,554 | 19 | ND | 18 |
| | | No Antigen | ND | ND | ND | ND |
| | | SP1-065 | 11,261 | 23 | ND | 30 |
| | | No Antigen | ND | ND | ND | ND |
| | | SP1-070 | 9,675 | 6 | ND | 24 |
| | | No Antigen | ND | ND | ND | ND |
| Microsphere Formulation | SP1-065 | SP1-007 | 8,242 | 23 | 10 | 12 |
| | | No Antigen | 63 | ND | 7 | 8 |
| | | SP1-065 | 11,683 | 11 | 18 | 13 |
| | | No Antigen | 63 | ND | 7 | 8 |
| | | SP1-070 | 11,828 | 16 | 12 | 4 |
| | | No Antigen | 63 | ND | 7 | 8 |

ND: Not Detected

These comparative results show that the slow release formulations utilizing microspheres as vehicle elicited a cytokine profile comparable to that obtained by use of liposomal vehicle in which the concentration of IFN-γ was substantially elevated over other cytokines.

An analysis of the antibody responses induced by the microsphere formulations of MUC1 peptide SP1-065 in mouse serum is shown in FIGS. 14A and 14B. Preimmune serum samples and immune serum samples collected 12 days after the second immunization were analyzed for IgG and IgM antibody responses at various dilutions by direct enzyme immunoassays and an absorbance at 405 nm using known methods. A mouse polyclonal antiserum generated by using SP1-7-KLH as the immunogen was used as a positive control sample. FIG. 14A shows the results of the IgG assay and FIG. 14B shows the results of the IgM assay at various dilutions by direct enzyme immunoassays. Results are shown as absorbance of 405 nm (background not subtracted).

Similar analysis of antibody responses were conducted for the IgG subtypes using enzyme immunoassay as described above, but using subtype specific secondary antibodies. As shown by the data summarized in FIGS. 15A–15D, the test serum gave a positive response (higher than preimmune serum) only for IgG$_{2b}$ subtype (as shown in FIG. 15C), indicating a Th1 type response.

The foregoing description of the invention is exemplary for purposes of illustration and explanation. It should be understood that various modifications can be made without departing from the spirit and scope of the invention. Accordingly, the following claims are intended to be interpreted to embrace all such modifications.

What is claimed is:

1. A method of eliciting a Th1 specific immune response in a subject to a neoplastic disorder effectively treated by a Th1 specific immune response, comprising administering to the subject an immunostimulating amount of a composition comprising:

a) a liposome containing an immunogenically effective amount of a peptide consisting of a 11 to 34 amino acid sequence wherein said sequence contains at least one T cell epitope from the tandem repeat region of MUC1 core peptide; and the liposome of a), further including monophosphoryl lipid A.

2. The method of claim 1, wherein the liposome releases the peptide at a rate in the range of from about 10 to 2 weight percent over a 24 hour period at 37° C.

3. The method of claim 1, wherein the liposome is a multilamellar liposome.

4. The method of claim 1, wherein the monophosphoryl lipid A is administered in a dose range from about 920 ng to 39 ug.

5. The method of claim 1, wherein monophosphoryl lipid A is on the surface of the liposome.

6. The method of claim 1, wherein the neoplastic disorder is selected from the group consisting of breast, pancreatic and ovarian carcinomas.

7. The method of claim 1, wherein the peptide is a peptide as set forth in SEQ ID NO:1, SEQ ID NO:5 or SEQ ID NO:6.

8. The method of claim 7, wherein the peptide is a lipopeptide.

9. A method of eliciting a Th1 specific immune response in a subject to a neoplastic disorder effectively treated by a Th1 specific immune response, comprising administering to the subject an immunostimulating amount of a composition comprising:

a) a microsphere containing an immunogenically effective amount of a peptide consisting of a 11 to 34 amino acid sequence wherein said sequence contains at least one T cell epitope from the tandem repeat region of MUC1 core peptide; and the microsphere of a), further including monophosphoryl lipid A.

10. The method of claim 9, wherein the monophosphoryl lipid A is on the surface of the colloidal dispersion system.

11. The method of claim 9, wherein the neoplastic disorder is selected from the group consisting of breast, pancreatic and ovarian carcinomas.

12. The method of claim 9, wherein the peptide is a peptide as set forth in SEQ ID NO:1, SEQ ID NO:5 or SEQ ID NO:6.

13. The method of claim 12, wherein the peptide is a lipopeptide.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 16 amino acids
       (B) TYPE: amino acid
       (D) TOPOLOGY: linear (ii) MOLECULE TYPE: peptide (vii) IMMEDIATE SOURCE:
       (B) CLONE: SP1-007 MUC1

(xi) SEQUENCE DESCRIPTION: SEQ ID NO:1:

Gly Val Thr Ser Ala Pro Asp Thr Arg Pro Ala Pro Gly Ser Thr Ala
 1               5                  10                  15

(2) INFORMATION FOR SEQ ID NO:2:

(i) SEQUENCE CHARACTERISTICS:
       (A) LENGTH: 24 amino acids
       (B) TYPE: amino acid
       (D) TOPOLOGY: linear (ii) MOLECULE TYPE: peptide (vii) IMMEDIATE SOURCE:
       (B) CLONE: SP1-020 mouse MUC1

(xi) SEQUENCE DESCRIPTION: SEQ ID NO:2:

Asp Ser Thr Ser Ser Pro Val His Ser Gly Thr Ser Ser Pro Ala Thr
 1               5                  10                  15

Ser Ala Pro Glu Asp Ser Thr Ser
            20

(2) INFORMATION FOR SEQ ID NO:3:

(i) SEQUENCE CHARACTERISTICS:
       (A) LENGTH: 20 amino acids
       (B) TYPE: amino acid
       (D) TOPOLOGY: linear (ii) MOLECULE TYPE: peptide (vii) IMMEDIATE SOURCE:
       (B) CLONE: SP1-023 MUC1

(xi) SEQUENCE DESCRIPTION: SEQ ID NO:3:

Pro Asp Thr Arg Pro Ala Pro Gly Ser Thr Ala Pro Pro Ala His Gly
 1               5                  10                  15

Val Thr Ser Ala
            20

(2) INFORMATION FOR SEQ ID NO:4:

(i) SEQUENCE CHARACTERISTICS:
       (A) LENGTH: 17 amino acids
       (B) TYPE: amino acid
       (D) TOPOLOGY: linear (ii) MOLECULE TYPE: peptide (vii) IMMEDIATE SOURCE:
       (B) CLONE: SP1-037 PVA323-337

(xi) SEQUENCE DESCRIPTION: SEQ ID NO:4:

Ile Ser Gln Ala Val His Ala Ala His Ala Glu Ile Asn Glu Ala Gly
 1               5                  10                  15

Arg (2) INFORMATION FOR SEQ ID NO:5:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (vii) IMMEDIATE SOURCE:
        (B) CLONE: SPQ-065 MUC1

(xi) SEQUENCE DESCRIPTION: SEQ ID NO:5:

Thr Ala Pro Pro Ala His Gly Val Thr Ser Ala Pro Asp Thr Arg Pro
 1               5                  10                  15

Ala Pro Gly Ser Thr Ala Pro Pro
            20

(2) INFORMATION FOR SEQ ID NO:6:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (vii) IMMEDIATE SOURCE:
        (B) CLONE: SP1-070 MUC1

(xi) SEQUENCE DESCRIPTION: SEQ ID NO:6:

Arg Pro Ala Pro Gly Ser Thr Ala Pro Pro Ala His Gly Val Thr Ser
 1               5                  10                  15

Ala Pro Asp Thr Arg Pro Ala Pro Gly Ser Thr Ala Pro Pro
            20                  25                  30

(2) INFORMATION FOR SEQ ID NO:7:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (vii) IMMEDIATE SOURCE:
        (B) CLONE: HbcAg (xi) SEQUENCE DESCRIPTION: SEQ ID NO:7:

Ile Arg Thr Pro Pro Ala Tyr Arg Pro Pro Asn Ala Pro Ile Leu
 1               5                  10                  15

(2) INFORMATION FOR SEQ ID NO:8:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (vii) IMMEDIATE SOURCE:

-continued

```
    (B) CLONE: SP1-072

(xi) SEQUENCE DESCRIPTION: SEQ ID NO:8:

Glu Ala Ile Gln Pro Gly Cys Ile Gly Gly Pro Lys Gly Leu Pro Gly
 1               5                  10                  15

Leu Pro Gly Pro
            20
```